United States Patent
Ling

(10) Patent No.: US 11,186,950 B2
(45) Date of Patent: Nov. 30, 2021

(54) EFFICIENT METHODS AND COMPOSITIONS FOR RECOVERY OF PRODUCTS FROM ORGANIC ACID PRETREATMENT OF PLANT MATERIALS

(71) Applicant: Pierson Capital Environmental (Beijing) Limited, Beijing (CN)

(72) Inventor: Feng Ling, Jilin (CN)

(73) Assignee: Pierson Capital Environmental (Beijing) Limited, Beijing (CN)

( * ) Notice: Subject to any disclaimer, the term of this patent is extended or adjusted under 35 U.S.C. 154(b) by 0 days.

(21) Appl. No.: 17/058,595

(22) PCT Filed: May 28, 2018

(86) PCT No.: PCT/CN2018/088698
§ 371 (c)(1),
(2) Date: Nov. 24, 2020

(87) PCT Pub. No.: WO2019/227285
PCT Pub. Date: Dec. 5, 2019

(65) Prior Publication Data
US 2021/0131033 A1    May 6, 2021

(51) Int. Cl.

| | | |
|---|---|---|
| B01D 1/26 | (2006.01) | |
| D21C 11/00 | (2006.01) | |
| B01D 1/00 | (2006.01) | |
| B01D 3/14 | (2006.01) | |
| B01D 3/38 | (2006.01) | |
| B04B 11/02 | (2006.01) | |
| B04B 11/08 | (2006.01) | |
| C05F 5/00 | (2006.01) | |
| C07G 1/00 | (2011.01) | |
| C08B 1/08 | (2006.01) | |
| C08L 5/14 | (2006.01) | |
| C12F 3/10 | (2006.01) | |
| D21C 9/00 | (2006.01) | |

(52) U.S. Cl.
CPC ........ *D21C 11/0007* (2013.01); *B01D 1/0041* (2013.01); *B01D 1/26* (2013.01); *B01D 3/146* (2013.01); *B01D 3/148* (2013.01); *B01D 3/38* (2013.01); *B04B 11/02* (2013.01); *B04B 11/08* (2013.01); *C05F 5/008* (2013.01); *C07G 1/00* (2013.01); *C08B 1/08* (2013.01); *C08L 5/14* (2013.01); *C12F 3/10* (2013.01); *D21C 9/007* (2013.01)

(58) Field of Classification Search
USPC .......................................................... 162/29
See application file for complete search history.

(56) References Cited

U.S. PATENT DOCUMENTS

| | | | | |
|---|---|---|---|---|
| 4,746,401 | A * | 5/1988 | Roberts | D21C 3/222 162/72 |
| 8,968,515 | B2 * | 3/2015 | Balan | C12P 19/14 162/29 |
| 9,650,687 | B2 * | 5/2017 | Jansen | C07G 1/00 |
| 2012/0116063 | A1 * | 5/2012 | Jansen | C08H 8/00 530/507 |
| 2014/0162345 | A1 * | 6/2014 | Eyal | C11D 3/38618 435/253.6 |

FOREIGN PATENT DOCUMENTS

| | | |
|---|---|---|
| WO | 2000/068494 A1 | 11/2000 |
| WO | 2003/014467 A2 | 2/2003 |
| WO | 2009/092749 A1 | 7/2009 |
| WO | 2010/006840 A2 | 1/2010 |
| WO | 2011/154293 A1 | 12/2011 |

OTHER PUBLICATIONS

International Search Report of PCT/CN2018/088698 dated Feb. 27, 2019.
Written Opinion of PCT/CN2018/088698 dated Feb. 27, 2019.

* cited by examiner

*Primary Examiner* — Mark Halpern
(74) *Attorney, Agent, or Firm* — Much Shelist, PC; Christopher M. Cabral

(57) ABSTRACT

Provided are compositions and processes concerning efficient downstream processing of products derived from organic acids pretreatment of plant materials.

15 Claims, 14 Drawing Sheets

EFFICIENT METHODS AND COMPOSITIONS FOR RECOVERY OF PRODUCTS FROM ORGANIC ACID PRETREATMENT OF PLANT MATERIALS

This application is a 371 of PCT/CN2018/088698 filed on 28 May 2018.

FIELD OF THE INVENTION

The invention is related to compositions and processes concerning; (i) recovery of organic acids from a cellulosic pulp derived from organic acids pretreatment of plant materials, (ii) treatment of cellulose recovered from a cellulosic pulp derived from organic acids pretreatment of plant materials prior to conversion to glucose, (iii) separating and cleaning lignin from a lignin suspension derived from organic acids pretreatment of plant materials, (iv) recovery of organic acids from the aqueous phase of organic acids pretreatment of plant materials, (v) recovery of residual organic acids from hemicellulose-containing fractions derived from organic acids pretreatment of plant materials, and (vi) organic fertilizer produced from cellulose and hemicellulosic juice derived from organic acid pretreatment of plant materials.

BACKGROUND OF THE INVENTION

The invention relates in a first aspect to a method for recovering organic acids from cellulosic pulp by a combined application of dryer and desolventizer. This aspect of the invention increases efficiency of existing organic acids pretreatment process by allowing recovery and reuse of the organic acids used to dissolve the hemicellulose and lignin contained in lignocellulosic plant materials. After the dissolving step of organic acids pretreatment of plant materials, a mixture of soluble and insoluble parts is obtained. After separating the mixture into soluble and insoluble fraction, a cellulosic pulp and extraction liquor are obtained. The cellulosic pulp represents about 62% of the soluble fraction primarily composed of organic acids and water and 38% of the insoluble fraction primarily comprised of undissolved cellulose.

Organic acids pretreatment processes suitable to application of the present invention are described in international patent publications WO 2011/154293 and WO 2010/006840, the contents of which are hereby incorporated in their entirety. The present invention may also concerns recovery of organic acids from an organic acids pretreatment process step involving partial elimination of lignins to obtain a residual overall level of lignins of 0.3% to 4%. Such step is described in international patent publication WO 2012/049054, the contents of which is hereby incorporated in its entirety.

In such processes, the lost organic acids represent not only a significant portion of the unit operational costs, but the unrecovered organic acids also have an impact on environmental considerations. Thus, efficient recovery of organic acids from the cellulosic pulp produced by organic acids pretreatment of plant materials provides both economic and environmental advantages over existing methods.

In another aspect, the invention further relates to a process for treating cellulose by a combination of neutralization and alkalization, wherein the cellulose is derived from existing processes for producing bioethanol or other products, comprising organic acids pretreatment of plant materials. Such existing processes are described in U.S. patent publication 2013-0183733, the contents of which is hereby incorporated in its entirety.

Production of bioethanol via processes including the steps of organic acids pretreatment, involves an initial step to destructure lignocellulosic plant material by subjecting it to a mixture of formic acid, acetic acid and water, the next step involves separating cellulose from the other materials. In order to achieve the best possible yield of enzymatic hydrolysis of the separated cellulose, a partial elimination of lignin prior to the enzymatic hydrolysis step is disclosed, such a treatment of the cellulose, so as to eliminate the lignins in order to achieve a preferred lignin level, wherein the residual overall level of lignins is equal to approximately 1.65%, is carried out by means of treating cellulose with sodium hydroxide, followed by a washing step intended to eliminate the residual sodium hydroxide before enzymatic hydrolysis.

Typically, treatment of cellulose derived from organic acids pretreatment of plant materials is carried out by adding sodium hydroxide into the cellulose directly to adjust the pH to pH 10 to pH 12, subsequently a separation step is carried out to separate the mixture into the treated cellulose and the filtrate (mainly contain the sodium hydroxide and other soluble fractions). The cellulose produced by the existing organic acids pretreatment process, contains residual organic acids from the pretreatment process ranges between 0.5% to 5% of the dry cellulose by weight. Neutralization of these residual acids consumes large quantities of sodium hydroxide which directly result a cost increases for bioethanol production and indirectly results in cost increases for treatment of the filtrate. Thus, a method for minimizing the amount of sodium hydroxide required to reach the operational pH range prior for subsequent treatment of cellulose represents a particularly important advantage over existing methods.

In another aspect the invention relates to a process for separating and cleaning lignin from a lignin suspension derived from organic acid pretreatment of plant materials by use of centrifugation.

The organic acids pretreatment process uses an organic acids solution as reagent to dissolve the hemicellulose and lignin contained in plant materials, after separation, the extracted liquor is separated from the mixture. The extracted liquor which is composed primarily of cellulose, dissolved hemicellulose, lignin, minerals, organic acids, water and the others is concentrated by an evaporation system to remove part of the organic acids and water to a dry matter content of 55% to 65%, calculated from the total weight of the concentrated extraction liquor. The existing processes are described in international patent publications WO 2000/068494, WO 2009/092749, WO 2011/154293, and WO 2015/185639, the contents of each which are incorporated by reference in their entirety.

In such processes, a lignin suspension is typically obtained by dispersing the lignins in the mixture of concentrated extraction liquor and water and the separation of the lignin and sugars present in the lignin suspension are separated via a filter press. After separating the lignin, a pressed cake of lignin and sugar-comprising liquor are obtained. The pressed lignin cake is washed with water, or by a combination of air and water, to obtain a final washed lignin and washing liquor.

However, the filter press cannot run continuously throughout the entire process, and therefore washing the cake using a filter press cannot produce a homogeneous product due to structural limitations of the device. The filtered cake of lignin is a rectangle so that the wash path across the lignin cake is variable and generally inconsistent. The present disclosure provides methods for centrifugal recovery of lignins thereby reducing water usage and thus reducing energy consumption while improving recovery of lignin from lignin suspensions.

In another aspect the invention relates to a process for producing hemicellulosic juice by a combination of evaporation and stripping from the hemicellulosic mixture produced by organic acids pretreatment of plant materials which is comprised largely of dissolved hemicellulose, organic acids and water. The organic acids pretreatment process use the organic acids solution as a reagent to dissolve the hemicellulose and lignin contained in the lignocellulosic raw material in a relatively low temperature and atmospheric pressure, even in the following extraction liquor treatment process are carried out in a relatively low temperature and at an atmospheric or vacuum pressure so as to prevent furfural to be created.

Typically, the extraction liquor which consists of dissolved hemicellulose, lignin, organic acids and water is concentrated by the multi-effect evaporation system to remove part of the organic acids and water to a dry matter content of 55% to 65%, calculated from the total weight of the concentrated liquor. The lignin contained in the concentrated liquor is separated by an existing process for the separation of lignins and sugars from an extracted liquor, in this process, prior to separation of lignins and sugars, mixing the concentrated liquor with water in equal parts by weight, the separated lignin must be washed by water to remove the residual sugars, organic acids, the whole soluble materials and waters are collected together to form the hemicellulosic mixture of dissolved hemicellulose, organic acids and water produced in this process. Such processes are described in international patent publications WO 2011/154293 and WO 2010/006840, the contents of each which are incorporated in their entirety.

Dissolved hemicellulose in the hemicellulosic mixture mainly comprises xylose and arabinose which can be used to produce ethanol and other industrial products. However, organic acids present in the hemicellulosic mixture will inhibit conversion of xylose and arabinose to ethanol and other industrial products. Thus, efficient removal of organic acids from the hemicellulosic mixture to produce the hemicellulosic juice is particularly important for maximizing yield of ethanol from the available sugars within the hemicellulosic juice.

In another aspect the invention relates to recovering organic acids from the high water content organic acids solutions produced by organic acids pretreatment of plant materials processes. Typically the content of organic acids in such processes are higher than 83% of the total weight of the solution. The organic acids serve as reagent to dissolve the hemicellulose and lignin contained in the lignocellulosic raw materials in a relatively low temperature and atmospheric pressure to avoid production of furfural during the pretreatment process. After separation, the liquor containing dissolved hemicellulose, lignin, organic acids, water and other constituents. The water, constituted of the waters in the organic acids solution and in the raw material, is concentrated by an evaporation system to remove part of the organic acids with water which form the first stream of high water content organic acids solution.

The lignin contained in the concentrated liquor is separated by an existing process for the separation of lignins and sugars from extracted liquor in this process, prior to the separation of lignins from the concentrated liquor, mixing the concentrated liquor with water precipitates the lignins in the concentrated liquor, in equal parts by weight of the concentrated liquor. Subsequently, the separated lignin is washed with water to remove residual sugars, organic acids and other water soluble components.

The whole soluble materials with the waters, the water remained in the concentrated liquor, the water mixed in the concentrated liquor for precipitating the lignin, and the water used as washing water, are collected together to form a mixture consisting primarily of dissolved hemicellulose, organic acids, the water (remained and added in the process) and other minor components. Such processes are described in international patent applications WO 2011/154293 and WO 2010/006840, the contents of each which are incorporated in their entirety.

In order to efficiently remove the organic acids from the high water content organic acid solutions regardless of their source, a process a combination of evaporation with stripping is disclosed. The disclosed process comprises a first pass multi-effect evaporator to evaporate the organic acids with water from the mixture partially, the condensate of the evaporator which mainly comprises organic acids and the water, forms the second stream of high water content organic acids solution.

The concentrated organic acids mixture from evaporator is fed to a stripping column wherein the organic acids are further removed to a content of less than 2%, the condensate from the stripping column forms the third stream of high water content organic acids solution.

The fourth stream of high water content organic acids is derived from recovery of organic acids from the cellulosic pulp which contains about 62% of the soluble part (which largely consists of organic acids and water), and about 38% of the insoluble part (which consists mainly of cellulose) by use of a desolventizer adapted to utilize steam to remove the residual organic acids from dried cellulosic pulp. In this aspect of the present invention the condensate from the desolventizer forms the fourth stream of high water content organic acids solution.

In order to recycle the organic acids and the waters to the organic acids pretreatment process, the additional waters of these four streams of high water content organic acids solution need to be removed from these four streams of high water content organic acids solution to meet the requirement of water content for extraction and delignification step.

In another aspect the invention relates to a method for producing organic fertilizers by utilizing stillage from cellulose and hemicellulosic juice.

This invention is based on organic acid pretreatment plant materials wherein the plant materials, particularly grain straw, serve as raw material. The separation of lignocellulosic raw materials into cellulose, hemicellulosic juice and lignin by the organic acid pretreatment process, hydrolysis and fermentation of cellulose and hemicellulosic juice, and conversion of most of the cellulose and hemicellulosic juice into ethanol are described in international patent application WO 2015/185639, the contents of which is hereby incorporated in its entirety.

Typically, in processes for producing fuel ethanol after fermentation, the mixture of fermented cellulose and hemicellulosic juice is fed to a mash column of distillation system, where the ethanol is extracted to produce the fuel ethanol. In such processes the residue is released from the bottom of the mash column. One consequence of the organic acid pretreatment process is that most of the nutritional constituents of the lignocellulosic raw material (protein, potassium, phosphate, etc.) is separated into the hemicellulosic juice, and mixed with the fermentation material (yeast, glycerol, etc.) as stillage. Use this stillage becomes a key problem, without a productive use, the stillage will be treated as waste, and treatment of such waste is costly. Under existing processes, there is no good method being proposed. This aspect of the present invention provides a process for decanting and evaporating the stillage solids to form the basis of a valuable organic fertilizer while simultaneously contributing vapor derived from the stillage liquid as a thermocouple to the to the stillage solids evaporation system thereby producing a thermodynamically efficient method of recovering and processing otherwise unproductive stillage.

SUMMARY OF THE INVENTION

A first aspect of the present invention discloses methods and compositions for efficient, thorough and economic recovery of organic acids from cellulosic pulp by a combination of dryer and desolventizer. The method comprises a first step which uses the dryer to reduce the organic acids to a content of 5% to 12%, calculated from the total weight of the dried cellulosic pulp. At this level it is difficult to further remove organic acids by continued drying. To overcome this defect, the invention comprises a second step wherein a desolventizer is used to further remove the organic acids using direct steam as the desolventizing medium to reduce the organic acid content to less than 2%, relative to the total weight of the desolventized cellulosic pulp.

Another aspect of the present invention is to provide a process and compositions for treating cellulose by a combination of neutralization and alkalization that uses the minimum of sodium hydroxide possible to prepare cellulose for enzymatic digestion and means of recycling the sodium hydroxide liquor from the alkalization step to the neutralization step, using the minimum sodium hydroxide to decrease the cost of bioethanol production and treatment of the attendant wastes.

Another aspect of the present invention provides lignin separation and cleaning process and compositions, using centrifugation which further comprises recycling specific portions of centrifugate and online washing to obtain pure lignin to decrease overall water consumption and obtain high quality lignin.

Another aspect of the invention is a process to efficiently and economically remove organic acids from the hemicellulosic mixture of dissolved hemicellulose, organic acids, and water by combining evaporation with stripping to produce a hemicellulosic juice composition. The process comprises in a first step a multi-effect evaporation system to partially evaporate the organic acids with water to a dry matter content of 40% to 70%, calculated from the total weight of the concentrated hemicellulosic juice. The process further comprises a second step wherein the concentrated hemicellulosic juice is fed to a stripping column wherein the organic acids are further removed to a content of less than 2%, calculated from the total weight of the hemicellulosic juice.

Another aspect of the present invention is a process for efficient and economic removal of water from high water content organic acids solutions by a process comprising multi-column distillation to produce a composition suitable for subsequent recycling within the organic acids pretreatment process. The process is characterized by a) adopting a two to five columns distillation system to recover the organic acids, and b) feeding fresh steam only into the first column of the multi-column distillation system, and c) providing the vapors released from previous columns to the subsequent columns as the thermal energy sequentially, and d) feeding one or more streams of high water content organic acids solutions into different columns within the multi-column system to balance the energy requirements for the columns comprising the distillation system, and e) adjusting the content of the organic acids in the condensate of the first column to minimize fresh steam consumption, and f) recycling the total organic acids and the total waters discharged from the multi-column distillation system into the overall process constituting organic acid pretreatment of plant materials, which can maximally reduce the energy, i.e., steam consumption for recovering of the organic acids, meantime can recycle the total organic acids and waters to the pretreatment process.

In another aspect of the present invention is a method to utilize the stillage of fermentation of cellulose and hemicellulosic juices to produce an organic fertilizer composition efficiently and economically. Stillage is rich in organic matter and nutrients which meet the requirements as an organic fertilizer. The organic fertilizer can improve quality of the soil as well as providing nutrients to plants e.g. grains. In contrast, chemical fertilizers can damage soil even while providing nutrients to the plants. Organic fertilizer is an important emerging direction for agriculture. This aspect of the present invention is characterized by the use of the stillage (fermentation by products) to produce valuable organic fertilizer by an efficient and economic method. The method comprises separating stillage by decanting to obtain a solid fraction of stillage and a thin stillage comprising more dilute fraction of stillage. The method further comprises concentrating the thin stillage by multi-effects evaporation system to obtain a concentrated stillage, mixing the solid fraction and concentrated stillage to obtain a mixture, drying said mixture by dryer to obtain the organic fertilizer, the vapor released from the dryer as the thermal energy of the multi-effect evaporation system, the fresh steam is fed to the multi-effect evaporation system as the supplementary thermal energy.

DETAILED DESCRIPTION OF THE INVENTION

Recovery of Organic Acids from Cellulosic Pulp

The first aspect of the present invention discloses methods and compositions for efficient, thorough and economic recovery of organic acids from cellulosic pulp by a combination of dryer and desolventizer. The organic acids and desolventized cellulosic pulp are produced by a process comprising the steps of:
  a) drying a cellulosic pulp produced from organic acids pretreatment of plant material in a dryer to remove the organic acids to a content of 3% to 18%, calculated from the total weight of the dried cellulosic pulp, and,
  b) capturing the vapor released from the dryer for use in the extraction liquor concentration system and other organic acids pretreatment operational systems as a source of thermal energy, and
  c) condensing the vapor in the extraction liquor concentration system and other organic acids pretreatment operational systems to form a first phase of the organic acids solution of the organic acids pretreatment process, and
  d) using direct steam in a desolventizer to further remove the organic acids from the cellulosic pulp, to a content of less than 2%, and
  e) condensing the organic acids vapor released from the desolventizer, to obtain a second phase of organic acids solution of the organic acids pretreatment process.

This aspect of the invention relates to a method for recovering organic acids from cellulosic pulp derived from the organic acids pretreatment process of plant material by a combination of dryer and desolventizer. The organic acids pretreatment process uses the organic acids as a reagent to dissolve the hemicellulose and lignin contained in the lignocellulosic plant materials. After separating the cellulosic pulp from the mixture of the soluble part and insoluble part, the residue which includes the insoluble part is the cellulosic pulp.

The existing organic acids pretreatment process may include a step of partial elimination of the lignins to obtain a residual overall level of lignins of 0.3 to 4% of the total cellulosic pulp by dry weight. The content of the organic acids in the cellulosic pulp may be 35% to 65%, calculated from the total weight of the cellulosic pulp. The content of the cellulose in the cellulosic pulp may be 30% to 50%, calculated from the total weight of the cellulosic pulp.

Figure 1:
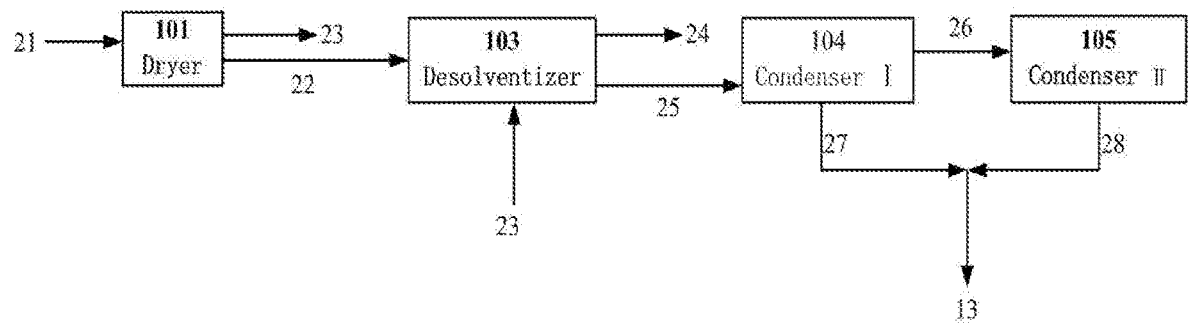
FIG. 1 is a process diagram illustrating how organic acids are recovered from cellulosic pulp by combination of dryer and desolventizer units. Cellulosic pulp (21) is introduced into the dryer unit (101) to obtain dried cellulosic pulp (22) and vapor (23). The vapor (23) is used to provide thermal energy to the extraction liquor concentration system as well as other operational units within the overall system. Dried cellulosic pulp (22) is fed to the desolventizer (103) to further remove organic acids by utilizing direct steam (23) as the desolventizing medium to obtain desolventized cellulosic pulp (24). The vapor (25) from the desolventizer unit is fed to condenser I (104). Non-condensing vapor (26) from condenser I (104) is fed to condenser II (105). The condensed vapor solution (27) from condenser I and the condensed vapor solution (28) from condenser II (105) may be combined to form the organic acids solution (13).

As shown in FIG. 1 the cellulosic pulp from the organic acids pretreatment process is fed to the dryer. The dryer reduces the organic acids to a content of 3% to 18%, calculated from the total weight of the dried cellulosic pulp, once the content of the organic acids is lower than 3%, the dryer cannot efficiently further remove organic acids, if the content of the organic acids is higher than 18%, the consumption of direct steam by the desolventizer is inefficient.

Drying of the cellulosic pulp is carried out by many forms of dryers which may include tube dryers, pneumatic dryers, spray dryers, rotary disc dryers, and other dryer technologies known to those in the art; it is particularly preferable to utilize a tube dryer. The dryer step may be carried out at a temperature of 90° C. to 150° C. After drying, the dried cellulosic pulp discharged from dryer is fed to the desolventizer.

The vapor which released from the dryer may be used for the extraction liquor concentration system as well as provide other systems with thermal energy. The condensates of the vapor from the dryer which is condensed in the extraction liquor concentration system and other systems form the first phase of organic acids solution and may be reused in the organic acids pretreatment process.

Figure 2:
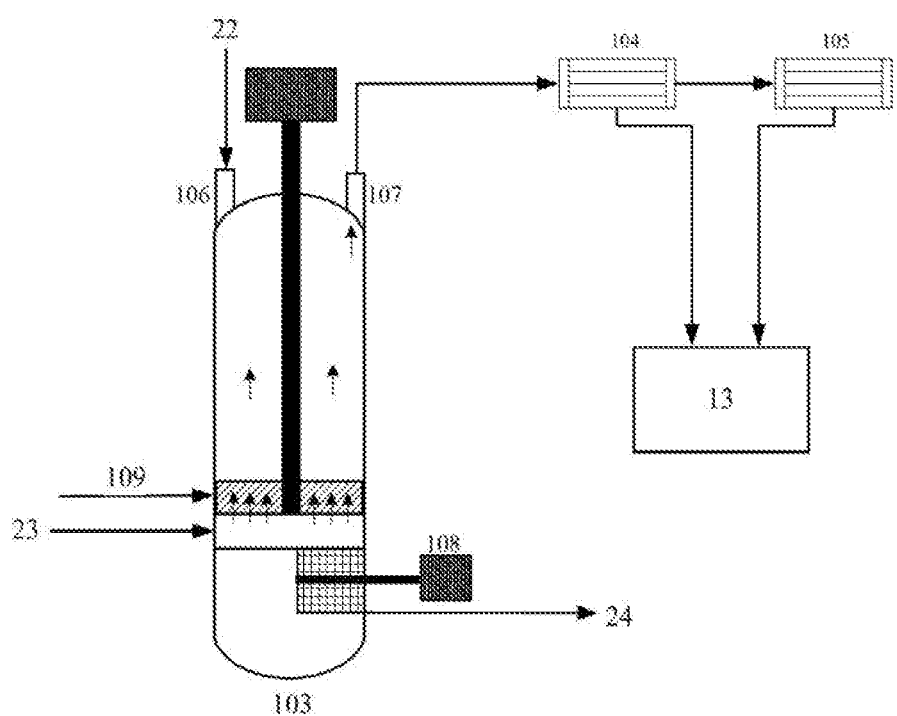
FIG. 2 is a schematic illustrating the structure of the desolventizer (103). Dried cellulosic pulp (22) is fed into the top of the desolventizer (103) through a feed inlet (106). The direct steam (23) sprays out from the holes of the plate (109) then goes out through the layer of the dried cellulosic pulp, meantime the direct steam brings the residual organic acids which is contained in the dried cellulosic pulp to form the organic acids vapor, the organic acids vapor is released from the vapor outlet (107) of the desolventizer (103). The released organic acids vapor is fed into condenser I (104) and the uncondensed vapor within Condenser I (104) is fed into condenser II (105). The condensates of condenser I (104) and condenser II (105) form the organic acids solution (13). After desolventizing, the desolventized cellulosic pulp (24) is discharged by a rotary discharger (108).

In the desolventizer shown in FIG. 2, the organic acids are further removed from the dried cellulosic pulp to a content of less than 2%, calculated from the total weight of desolventized cellulosic pulp. The desolventizer may utilize direct steam as the desolventizing medium to remove the organic acids furtherly from the dried cellulosic pulp. The desolventizer may further remove the organic acids by using direct steam as the desolventizing medium in step d) carried out at a temperature of 90° C. to 150° C.

After the desolventization step, the desolventized cellulosic pulp can be used to produce ethanol and other products.

The organic acids vapor also contains water released from the desolventizer is recovered by the condensation system of the organic acids distillation system, wherein the organic acids are recovered for use in the organic acids pretreatment process. The condensation system is carried out by 1 to 3 condensers, preferably by 2 condensers.

Production of Alkalized Cellulose

This aspect of the invention relates to a process for treating cellulose by a combination of neutralization and alkalization to produce an alkalized cellulose comprising the steps of:
  a) neutralizing the organic acids contained in the cellulose produced from organic acids pretreatment of plant material with sodium hydroxide liquor recycled from step d) of the process to form a neutralized cellulose mixture, and
  b) separating neutralized cellulose from the neutralized cellulose mixture with a press, the filtrate is directly released to waste water treatment system, and
  c) alkalizing the neutralized cellulose by addition of a sodium hydroxide solution in a reactor to form an alkalized cellulose mixture, and
  d) separating the alkalized cellulose from the alkalized cellulose mixture with a press, wherein the sodium hydroxide liquor (filtrate of the alkalized cellulose mixture) comprises sodium hydroxide for reuse in step a) of the process.

In this aspect of the invention, the cellulose produced from cellulosic pulp derived from the organic acid pretreatment processes and stripped of residual organic acids by the drying and desolventizing steps described above may still contain a residual level of organic acids representing is 0.5% to 5% of the total weight of the cellulose. In this aspect of the invention such cellulosic pulp is further treated to form an alkalized cellulose by a process comprising neutralization and subsequent alkalization.

Figure 3:
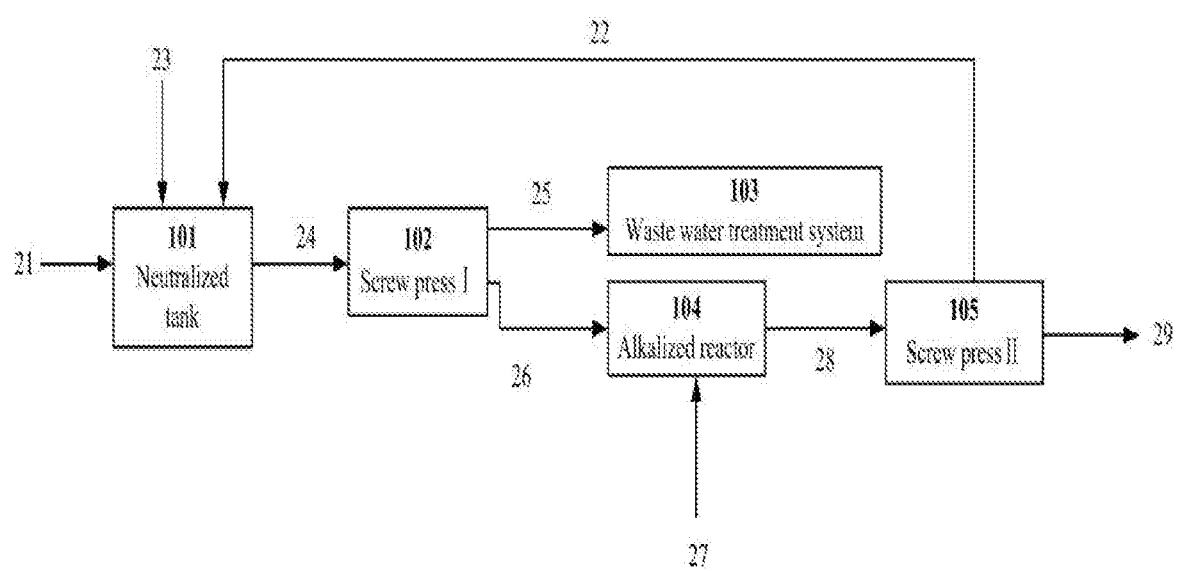
FIG. 3 is a schematic illustrating the treatment of cellulose by a combination of neutralization and alkalization wherein the cellulose (21) is fed to the neutralization tank (101) where sodium hydroxide (23) and recycled sodium hydroxide liquor (22) are added to form the neutralized cellulose mixture (24). The neutralized cellulose mixture (24) is fed into press I (102) to obtain a filtrate (25) and the neutralized cellulose (26). The filtrate (25) is discharged to a waste water treatment system (103), while the neutralized cellulose (26) is fed to the alkalized reactor (104). Within the alkalized reactor (104) sodium hydroxide (27) is added to obtain an alkalized cellulose mixture (28). The alkalized cellulose mixture (28) is fed into press II (105) to obtain the sodium hydroxide liquor (22) to recycle to the neutralization tank and the final alkalized cellulose (29) product.

As illustrated in FIG. 3, in step a) of the process residual organic acids contained in the cellulose are neutralized by adding sodium hydroxide liquor recycled from separating the alkalized cellulose from the alkalized cellulose mixture in step d). The pH of the sodium hydroxide liquor is pH 10 to pH 12. After addition of the sodium hydroxide liquor to the cellulose, the pH of the cellulose mixture is adjusted to a range of 5 to 8 by addition of more sodium hydroxide as necessary. Use of sodium hydroxide liquor recycled from the last steps of the process for producing alkalized cellulose can decrease the overall consumption of sodium hydroxide from 30% to 65% by weight, relative to current treatment processes.

In step b) the neutralized cellulose is separated from the neutralized cellulose mixture by use of a press. The press may be a screw press or other type of press known to those of skill in the art. In this separation step, the neutralized cellulose mixture formed in step a) is separated into two streams, one comprises the neutralized cellulose, the other comprises the filtrate. The neutralized cellulose has a dry solid content of 30% to 45%. The filtrate is directly released to a waste water treatment system, the pH of the filtrate is pH 5 to pH 8, so there is no need to adjust the pH by titration as in existing treatment processes.

In step c), the neutralized cellulose is alkalized by adding a sodium hydroxide solution to the neutralized cellulose in a reactor to a pH of pH 10 to pH 12, at a temperature of 50° C. to 100° C. Under these conditions the content of the lignin contained in the cellulose can be reduced to a level of 1% to 2.5%, calculated from the total weight of the cellulose.

In step d), the alkalized cellulose mixture is separated by use of a press. In this separation step, the alkalized cellulose mixture is separated into two streams, one stream comprises the alkalized cellulose, the other stream comprises the sodium hydroxide liquor.

The alkalized cellulose contains a dry solid content of 30% to 45%, calculated from the total weight of the alkalized cellulose. After a washing step, this alkalized cellulose can be hydrolyzed by cellulase with a high conversion rate of cellulose to glucose.

The sodium hydroxide liquor may be recycled for neutralizing the organic acids in step a).

Production of Pure Lignin

This aspect of the invention relates to a process for separating and cleaning lignin from a lignin suspension by precipitation and centrifugation, comprising the steps of:
- a) separating lignin from a lignin suspension produced from organic acids pretreatment of plant material by batch or continuous centrifugation, and
- b) cleaning the precipitated lignin in the centrifuge by multiple applications of wash solution onto the lignin layer during centrifugation, to form multiple centrifugates, and
- c) recovering a first centrifugate and a second centrifugate for use in hemicellulosic juice concentration, and
- d) recycling a third centrifugate for precipitating the lignin in the concentrated extraction liquor into lignin suspension of the organic acids pretreatment process.
- e) discharging the lignin from the centrifuge.

The extraction liquor of this aspect of the invention is obtained from existing organic acids pretreatment processes wherein the hemicellulose and lignin contained in plant materials are dissolved in the organic acids solutions from which the extraction liquor is derived. The extracted liquor is separated from the mixture, the extracted liquor which comprises cellulose, dissolved hemicellulose, lignin, minerals, organic acids, water and the other minor constituents is concentrated by the evaporation system to remove part of the organic acids and water to a dry matter content of 55% to 65%, calculated from the total weight of the concentrated extraction liquor.

Accord to the present invention, the separating equipment is a centrifuger, preferable a scraper centrifuger, which may be run in continuous or batch mode. The centrifuger is equipped with a spraying device which can evenly spray washing water onto the lignin layer to obtain a pure lignin.

Figure 4:
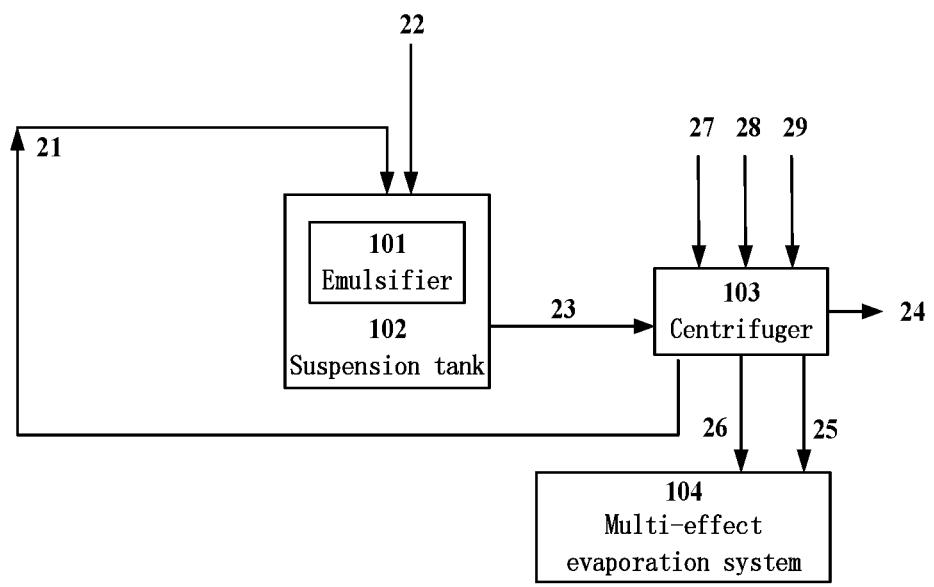
FIG. 4 is a process diagram illustrating a process for producing pure lignin. In this process the third centrifugate (21) mixes with concentrated extraction liquor (22) to form the mixture, the mixture is emulsified in the suspension tank (102) by using the continuous or batch emulsifier (101) to form stable lignin suspension (23). The lignin suspension (23) is then fed into a centrifuge (103) where the lignin suspension is separated into a lignin layer and a first centrifugate (25). The first centrifugate (25) is delivered to a multi-effect evaporation system (104) for hemicellulosic juice production. A first wash water (27) is introduced to wash the lignin layer to produce a second centrifugate (26). The first wash water may be the high acid content water from condenser I of the acids distillation unit (5) of FIGS. 10-13. The second centrifugate (26) is also delivered to the multi-effect evaporation system (104) for hemicellulosic juice production. A second wash water (28) is introduced to the lignin layer to produce at least a third centrifugate (21). The second wash water may comprise the low acids content wash water from the other condensers except condenser I of the acids distillation unit (7) of FIGS. 10-13, or fresh water (29), or a mixture of both. The third and any subsequent centrifugates may be combined and reintroduced into the suspension tank (102) to suspending the lignin. The washed lignin is discharged from the centrifuge as pure lignin (24).
Figure 5:
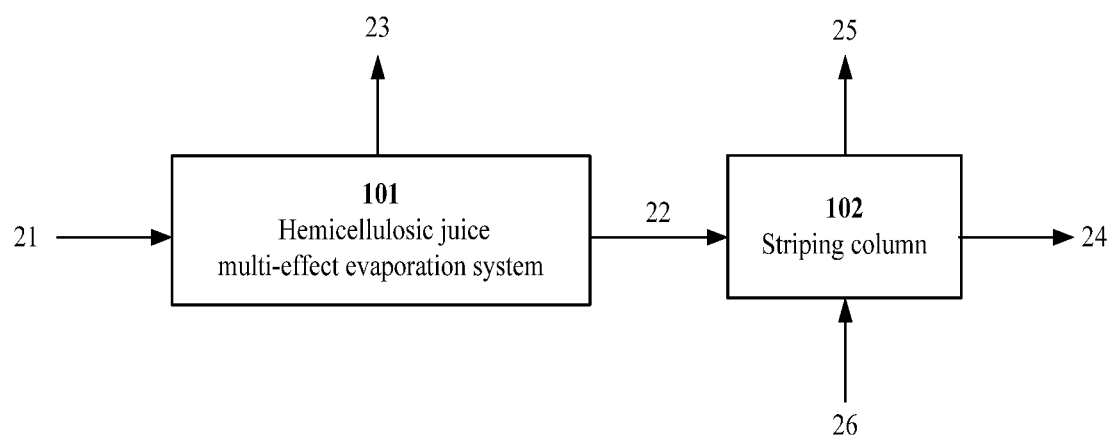
FIG. 5 illustrates the sequence of steps involved in producing hemicellulosic juice. Raw hemicellulosic juice (21) separated from extraction liquor by lignin precipitation, filtration, and washing is fed into a multi-effect evaporation system (101). A concentrated hemicellulosic juice (22) and condensed organic acids (23) are produced by the multi-effect evaporator system. Fresh steam (26) and the concentrated hemicellulosic juice (22) are introduced into the stripping column (102) to further remove organic acids and obtain the stripped hemicellulosic juice (24) with an organic acid content of less than 2% of the total weight of the stripped hemicellulosic juice and the newly condensed acids (25).

As illustrated in FIG. 4, the third centrifugate from step d) mixes with concentrated extraction liquor to form the mixture, the mixture is fed to the suspension tank in which the mixture is emulsified by using the continuous or batch emulsifier to form the stable lignin suspension. The lignin suspension is then successively fed to the centrifuge, the centrifuge then separates the lignin suspension to obtain the first centrifugate and a lignin layer. The first centrifugate which comprises 10% to 60% of the total centrifugate volume is recovered for subsequent processing by the hemicellulosic juice production unit.

The spraying device delivers washing water which may include a mixture of formic acid, acetic acid and water to provide an online wash of the lignin layer. In a preferred embodiment the centrifuge is continuously rotating. Under continuous rotation, the washing water can be evenly sprayed on the lignin layer to provide homogeneous cleaning of the lignin. During spraying, impurities are washed out by the washing water, the recovered washing water and the impurities form the second centrifugate which comprises 10% to 30% of the total centrifugate by volume. The centrifuge continues to operate while subsequent washes are applied to produce third and possible more centrifugates. The third and subsequent centrifugates may comprise 10% to 50% of total centrifugate by volume. Once the final centrifugate is removed the lignin layer is discharged from the centrifuger to obtain a pure lignin comprising 90% to 99% lignin by weight.

The washing water may comprise water or a mixture of formic acid, acetic acid and water, wherein the formic acid content of the mixture is 0% to 30%, calculated from the total weight of the mixture, and the acetic acid content of the mixture is 0% to 20%, calculated from the total weight of the mixture. The mixture of formic acid, acetic acid and water may derive from the recovered organic acids from high water content organic acids solutions by acids distillation unit. In a preferred embodiment the initial washing water introduced into the centrifuge are derived from the high organic acids content washing water. In some embodiments the second washing water introduced into the centrifuge are derived from the low organic acids content washing water. In some embodiments fresh water comprises the washing water for the third and any subsequent wash procedures for cleaning the lignin layer to obtain the pure lignin.

The first centrifugate and the second centrifugates may be recovered and delivered to the subsequent hemicellulosic juice production unit, while the third and any subsequent centrifugate may be recycled to the lignin suspending step to decrease water consumption for the initial lignin precipitation step which consequently decreases energy consumption of the hemicellulosic juice production and organic acids recovery unit.

Production of Hemicellulosic Juice

This aspect of the invention relates to a process for producing hemicellulosic juice by a combination of evaporation and stripping, comprising the steps of:
- a) introducing a hemicellulosic mixture comprised of dissolved hemicellulose, organic acids, water and others produced by organic acids pretreatment of plant material into a multi-effect evaporation system, and
- b) evaporating the hemicellulosic mixture within the multi-effect evaporator to form a concentrated hemicellulosic juice with a dry matter content of 40% to 70% (w/w), and c) removing organic acids from the concentrated hemicellulosic juice in a stripping column to form a hemicellulosic juice, wherein the hemicellulosic juice comprises less than 2% (w/w) organic acids.

This invention is based on the existing organic acids pretreatment of plant materials process, wherein a mixture of formic acid and acetic acid or formic acid only are used to dissolve hemicellulose and lignin from the lignocellulosic raw plant materials, after an initial separation step, the extraction liquor which comprises dissolved hemicellulose, lignin, organic acids, water and other minor constituents is separated from the remaining insoluble material (mainly comprising cellulose).

After lignin precipitation, filtration and washing steps, the lignin is removed from the extracted liquor, the remainder known as hemicellulosic juice is comprised of dissolved hemicellulose, organic acids, water and other minor water soluble constituents.

The dissolved hemicellulose in the hemicellulosic juice is mainly comprised of xylose and arabinose, which can be used to produce ethanol and other industrial products. Organic acids remaining in the hemicellulosic juice may inhibit the conversion of xylose and arabinose to ethanol and other industrial products. In addition, such organic acids represent a loss of a costly reagent in the overall organic acids pretreatment process. This aspect of the invention specifically concerns producing hemicellulose suitable for optimal conversion to ethanol with minimal residual organic acids by a process that can simultaneously recover such organic acids present in hemicellulosic juice for use in the organic acids pretreatment process.

The content of dissolved hemicellulose in hemicellulosic juice is 2% to 20%, calculated from the total weight of the hemicellulosic mixture. The content of organic acids in the hemicellulosic juice is 10% to 30%, calculated from the total weight of the hemicellulosic mixture. Step a) of the present invention is characterized in that the multi-effect evaporation system partially evaporates the organic acids with water to a dry matter content of 40% to 70%, calculated from the total weight of the concentrated hemicellulosic juice.

Figure 6:
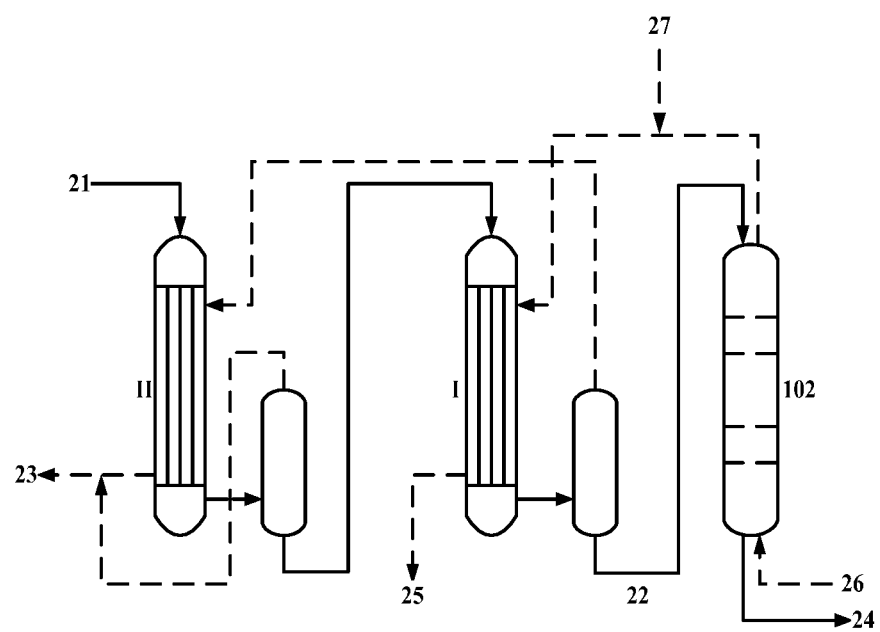
FIG. 6 graphically details a 2-effect evaporation and stripping system. Internal labels are described in Example 4.
Figure 7:
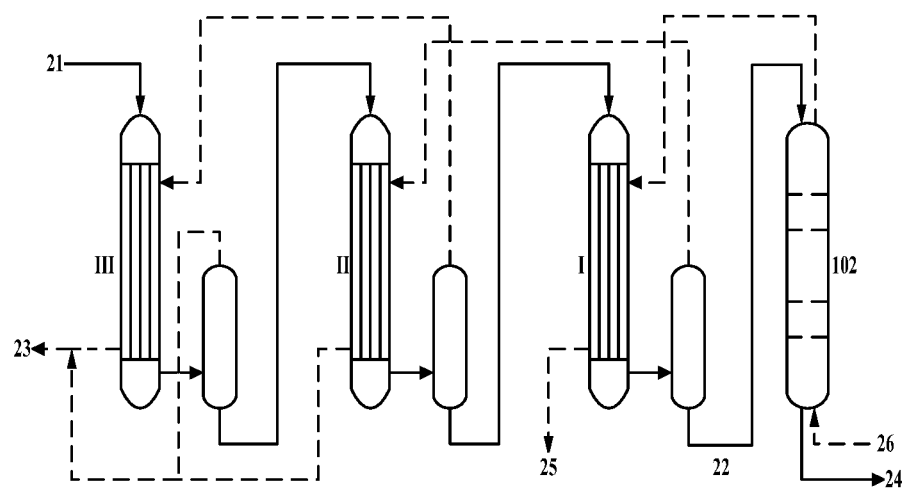
FIG. 7 graphically details a 3-effect evaporation and stripping system. Internal labels are described in Example 4.
Figure 8:
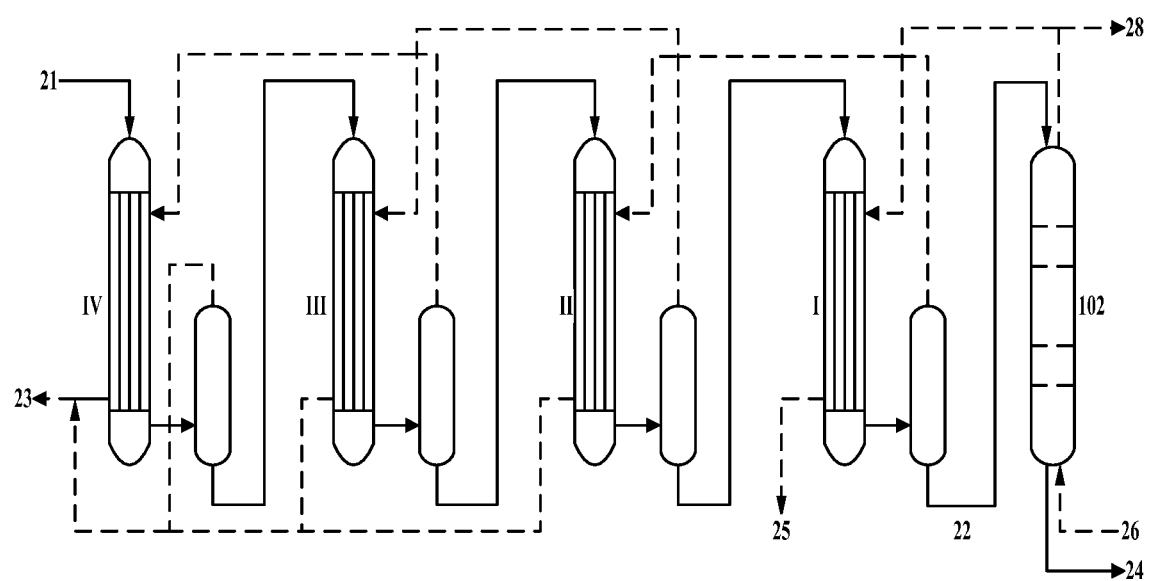
FIG. 8 graphically details a 4-effect evaporation and stripping system. Internal labels are described in Example 4.
Figure 9:
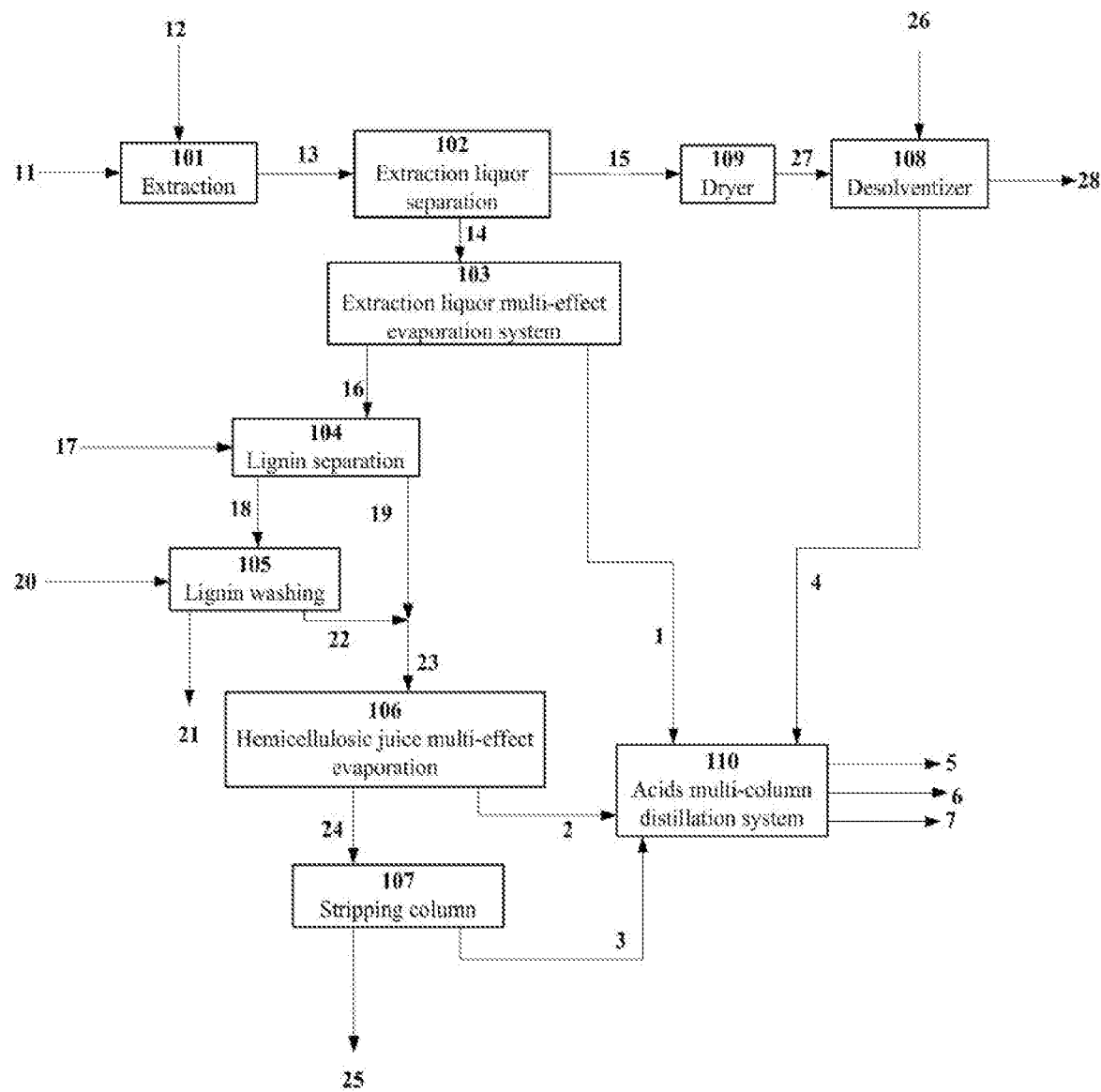
FIG. 9 is a flow diagram of the process for recovering organic acids from high water content organic acids solutions by multi-column distillation. Raw lignocellulosic plant materials (11) are fed to the extraction step (101). Organic acids (12) are added to the plant material at the extraction step (101) to dissolve the hemicellulose and lignin from the raw plant material (11) to obtain an extraction mixture (13). An extraction liquor (14) is produced by separation (102) of soluble and suspended particles from the extraction mixture wherein the insoluble and unsuspended residue comprise the cellulosic pulp (15). The cellulosic pulp (15) is dried in a dryer (109) to produce a dried cellulosic pulp (27) and the condensate from the dryer, including organic acids may be recycled in the extraction step (101). In this process, the extraction liquor (14) is fed into the evaporation system (103) to partially remove residual organic acids and water to form a first stream of high water content organic acids solution (1) and obtain concentrated liquor (16). The concentrated liquor (16) is fed into the lignin separation (104) step, in this step the addition of water (17) precipitates the lignin, allowing separation of the lignin from the concentrated liquor (16), obtaining the separated lignin (18) and the soluble materials with the waters (19). The lignin requires washing with various wash waters (20) in a series of lignin washing steps (22) to remove residual sugars, organic acids and other water soluble constituents. The water from the lignin washing step (105) and the soluble materials with the wash water (19) are pooled to form a mixture of hemicellulose, organic acids, water and other water soluble constituents (23). To remove the organic acids from this mixture (23) and reduce the water content the mixture (23) is subject to multi-effect evaporation (106) The condensate of the multi-effect evaporator forms a second stream of high water content organic acids solution (2). Following the multi-effect evaporation (106) the concentrated mixture (24) is fed into a stripping column (107) wherein the organic acids are further removed to a content of less than 2%, the condensate from the stripping column forms a third stream of high water content organic acids solution (3) and the hemicellulosic juice (25). To remove organic acids from the dried cellulosic pulp (15) a desolventizer (108) is adapted to use direct steam (26) to remove the residual organic acids. The condensate from the desolventizer forms a fourth stream of high water content organic acids solution (4) and the desolventized cellulosic pulp (28). The four streams of high water content organic acids solutions are fed into the multi-column distillation system (110) to reduce the water content. An aqueous acid solution (5) is obtained with an acid content of 0.5 to 10% in the condensate discharge from the top of the first column. Subsequent columns produce condensate (7) discharge with acid content of 0.2% to 1%. Aqueous acid solutions (6) with an acid content of 5% to 15% comprise the bottom output of the first column. Where all acid percentages are calculated by weight.

The multi-effect evaporation can decrease the steam/energy consumption for removing the organic acids and concentrating the hemicellulosic juice. In some embodiments the multi-effect evaporation is characterized by use of 2 to 4 effects evaporation systems as shown in FIGS. 6-8. In a preferred embodiment the process uses a 3 effects evaporation system.

In some embodiments the multi-effect evaporation of organic acids with water is carried out at a temperature of 60° C. to 160° C. in the first effect evaporator. In some embodiments the multi-effect evaporation of organic acids with water is carried out at a temperature of 25° C. to 60° C. in the last effect evaporator.

The first evaporator of the multi-effect evaporation system may utilize the vapor output from the top of the stripping column as the complete source or as a partial source of thermal energy. In each step of the multi-effect evaporation system, the vapor output from the top of the previous evaporator may be utilized for thermal energy to drive the following column to reduce the overall energy required by the multi-effect evaporation system.

As shown in FIGS. 6-8 the hemicellulosic mixture is fed in the first evaporator and discharged from the first evaporator sequentially.

After the concentration of the hemicellulosic juice by the multi-effect evaporation system, the dry matter content of concentrated hemicellulosic juice which is discharged from the first evaporator is 40% to 70% of the total weight of the concentrated hemicellulosic juice, the viscosity of the concentrated hemicellulosic juice is 200 mPas to 1000 mPas, if the viscosity is higher than this range, the concentrated hemicellulosic juice it is too difficult to further remove the organic acids by evaporation.

This invention is further characterized by combining the multi-effect evaporation system with a stripping column. The concentrated hemicellulosic juice discharged from the multi-effect evaporation system is fed to the top plate of the stripping column. The stripping column utilizes direct steam as the stripping medium to remove the organic acids further to a content of less than 2% of the total weight of the stripped hemicellulosic juice.

The vapor output from the top of the stripping column may be used as the thermal energy of the first evaporator of the multi-effect evaporation system.

The stripped hemicellulosic juice discharged from the bottom of the stripping column is used as the final product, i.e. the hemicellulosic juice, which can be used to produce ethanol and other industrial products.

Removal of Water from High Water Content Organic Acids Solutions

This aspect of the invention relates to a process for recovering organic acids from high water content organic acids solutions by multi-column distillation, comprising,
 a) adopting a two to five columns distillation system to recover the organic acids, and
 b) feeding fresh steam only into the first column of a multi-column distillation system, the others columns utilize the vapor released from the previous column as the thermal energy sequentially, and
 c) directing the vapors released from previous columns to the subsequent columns as the thermal energy, so that the vapor released from the first column will be fed into the second column and the vapor released form the second column will be fed into third column and so on through each column of the distillation system, and
 d) feeding one or more streams of high water content organic acids solutions into different columns within the multi-column system to balance the energy requirements for the columns comprising the distillation system, and
 e) adjusting the content of the organic acids in the condensate of the first column to minimize fresh steam consumption, and
 f) recycling the total organic acids and the total waters discharged from the multi-column distillation system.

In this aspect of the invention, the high water content organic acids solutions derived from organic acids pretreatment process of plant material. Typically the content of the organic acids comprises more than 83% of the total weight of the solution. Typically, during the organic acids pretreatment process, and as a consequence of the downstream steps of cellulosic pulp processing and lignin and hemicellulosic sugar production in a relatively low temperature and atmospheric pressure, which lead to that there is no furfural created during the whole pretreatment process, as well as four streams of high water content organic acids solutions are generated. In order to recycle the organic acids in the high water content organic acids streams into the organic acids pretreatment process the water content must be reduced.

Recovering organic acids from the high water organic acids solution by distillation requires very high energy inputs. Therefore, reducing the energy required to recover and recycle organic acids is essential for commercializing the organic acids pretreatment process.

In one embodiment the invention is characterized in that recovering organic acids from high water content organic acids solution by use of a two to five column distillation system to maximize energy efficiency. A preferred embodiment uses a four column distillation system.

The greater the number of columns, the less steam/energy is consumed by the distillation system. However, the number of columns comprising the distillation system is limited by the difference of temperature between the columns of the distillation system. Surprisingly, we have empirically discovered that if the system includes more than five columns the difference in temperature between the columns is too small to use the vapor released from the previous column as the steam/energy for the following column in series.

After scientific analysis, two to five columns distillation system can be suitable for recovering organic acids from high water content organic acids solution in this process, four columns distillation is the most suitable from the view of efficiency and economy.

Typically, organic acids pretreatment processes create four streams of high water content organic acids solutions as described above. The term "high water content organic acids solution" means the water content is higher than the required water content in the organic acids solution used for dissolving plant materials in the organic acids pretreatment process. Thus, to recycle the organic acids from the four high water content organic acids streams, the additional water added throughout the various process steps needs to be removed. In order to minimize the amount of steam/energy required for recovering organic acids from high water content organic acids solutions by multi-column distillation it is necessary to regulate the steam/energy used for each column so that it is suitable to the level of organic acids within the individual column within the series.

The invention adopts two methods to accomplish this. First by feeding the highest water content organic solution to the last column of the distillation system and feeding the lowest water content organic acids solution to the first column of the distillation system the energy input into the entire system is directed appropriately. Second, by regulating the organic acids content in the condensate discharged from the top of first column from 0.5% to 10% of the total weight of the condensate by adjusting the quantity of the steam/energy introduced into the first column allows the consumption of the steam/energy across the whole distillation system to be balanced. The condensate of the first column organic acids content of 0.5% to 10% can be diverted for use in the lignin precipitation step of the lignin production process.

In the system described here other columns in the series typically produce condensates with an organic acids content of 0.2% to 1% of the total weight of the input condensates. These condensates can be recycled to the pretreatment process for washing lignin and other steps in the lignin production process.

In order to maintain an optimal temperature differential between the columns, the first column is operated out at a temperature of 120° C. to 175° C., the last column is operated at a temperature of 50° C. to 95° C.

The organic acids solution discharged from the bottom of the first column has a water content of 5% to 15%, calculated from the total weight of the organic acids solution, these organic acids solution can be directly reused to the organic acids pretreatment process at the initial step of solubilizing the raw plant material.

Organic Fertilizer

Figure 14:
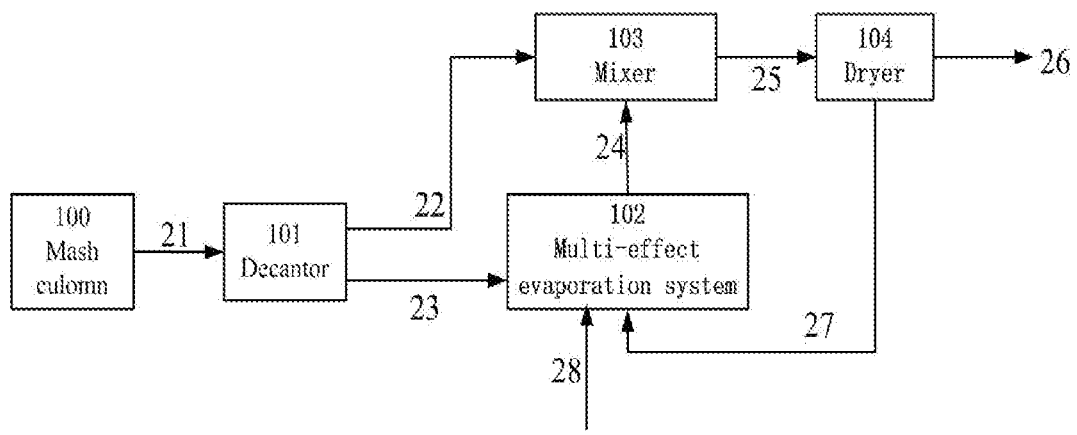
FIG. 14 is a process diagram illustrating production of an organic fertilizer from fermentation stillage (21) from the bottom of a mash column (100) of an ethanol distillation system. The stillage (21) is fed into a decanter (101) to obtain a solid fraction (22) and a thin stillage (23). The thin stillage (23) is fed to the multi-effect evaporation system (102) to generate a concentrated stillage (24). The solid fraction (22) and the concentrated stillage (24) are fed into a mixer (103) wherein the two fractions are mixed to obtain a mixture (25). The mixture (25) is fed into a dryer (104) to obtain a dried mixture (26) and this dried mixture (26) represents a high quality organic fertilizer. The vapor (27) released from the dryer (104) may be fed into the multi-effect evaporator (102) to provide thermal energy for the evaporation process, the fresh steam (28) is fed to the multi-effect evaporation system (102) as the supplementary thermal energy.

This aspect of the invention depicted in FIG. 14 relates to a method for producing organic fertilizer from stillage created from cellulose and hemicellulosic juice, comprising the steps of:

a) separating stillage from cellulose and hemicellulosic juice produced by organic acids pretreatment of plant material using a decanter to obtain a solid fraction of the stillage and a thin stillage, and b) concentrating the thin stillage with a multi-effect evaporation system to obtain a concentrated stillage wherein the steam for the multi-effect evaporation system is supplied from vapor released from the dryer in step d) of the process optionally supplemented with fresh steam, and c) mixing the solid fraction and concentrated stillage to obtain a mixture, and d) drying the mixture to obtain the organic fertilizer, wherein the vapor released from the dryer is fed to the multi-effect evaporation system as thermal energy for the multi-effect evaporation system of the process.

This invention is based on the existing organic acids pretreatment process. In the pretreatment process, the organic acids solution is used as the extraction reagent to dissolve most of the lignin, hemicellulose, salts (mainly salts of potassium and the phosphate), protein and the other components of the lignocellulosic plant materials. The pretreatment mixture is separated into the insoluble cellulosic pulp and a mixture of hemicellulosic juice and lignin. The cellulosic pulp is dried to obtain cellulose. The hemicellulosic juice and lignin mixture is separated into hemicellulosic juice (containing hemicellulose, salts, protein and the other soluble constituents) and lignin. After hydrolysis and fermentation of cellulose and hemicellulosic juice, most of the cellulose and the hemicellulose included in the hemicellulosic juice are converted into ethanol. After extraction of ethanol from the fermented cellulose and hemicellulosic juice by distillation, residues of fermented cellulose and hemicellulosic juice are discharged from the bottom of the mash column of the distillation system. The residues are the stillage (by-product of the process).

The stillage contains many of the nutritive components (protein, potassium, phosphorus, calcium, magnesium, sodium, aluminum, etc.) from the lignocellulosic raw materials as well as additional nutritive components comprising yeast, secondary metabolites produced by growth of the yeast during the fermentation, and residual yeast growth media including significant amounts of nitrogen, potassium, phosphorus and organic substances. Such material represents all the requirements of an organic fertilizer. Organic fertilizers are fertilizers derived from animal matter, animal excreta (manure), human excreta, and vegetable matter (e.g., compost and crop residues), in contrast, the majority of fertilizers used in commercial agriculture are chemical fertilizers extracted from minerals (e.g., phosphate rock) or produced industrially (e.g., ammonia). Organic agriculture, as a system of farming, allows for use of certain fertilizers and amendments and disallows others. Both organic and chemical fertilizers can provide significant boosts in plant yields however, organic fertilizers have more complete mineral profiles and cannot cause the kind of soil damage that can be inflicted by chemical fertilizers. Organic fertilizers are an important developing direction for agriculture.

This process disclosed here in one embodiment uses agriculture residues as the raw materials and the stillage produced in part by hydrolysis of cellulose and hemicellulose recovered from the agriculture residues and fermentation of the sugars released by hydrolysis of cellulose and hemicellulose by yeast to produce an organic fertilizer.

The method is characterized in that the stillage is obtained from the bottom of the mash column of an ethanol distillation system. The dry matter content is 2% to 20%, calculated from the total weight of the stillage. In one embodiment a centrifuge is used to separate the stillage into a solid fraction and a thin stillage fraction. In a preferred embodiment the centrifuge is a decanter centrifuge.

After separation, the dry matter content of the solid fraction is 20% to 45%, calculated from the total weight of the solid part of stillage. The dry matter content of the thin stillage fraction is 1% to 15%, calculated from the total weight of the thin stillage.

The thin stillage may be concentrated by a multi-effect evaporation system. The multi-effect evaporation system may include 4 to 6 effects evaporation system. In a preferred embodiment the multi-effect evaporation is a 5 effects evaporation system. In the multi-effect evaporation system, the vapor released from the top of the previous evaporator is utilized as the thermal energy of the following evaporator to minimize the total energy for the multi-effect evaporation system. The thin stillage is fed into the last evaporator of the multi-effect evaporation system and discharged from the first evaporator of the multi-effect evaporation system. The multi-effect evaporation system is carried out at a temperature of 30° C. to 150° C.

After the concentrating, the dry substance content of the concentrated stillage is 28% to 45%, calculated from the total weight of the concentrated stillage.

The condensate of the vapor separated in the multi-effect evaporation system, which is obtained in step b), may be reused as process water.

The solid part and concentrated stillage are fed to a mixer, wherein the two parts are mixed to obtain the mixture of the solid fraction and the concentrated stillage. The mixture of the solid part and the concentrated stillage is dried by the dryer, preferably the tube dryer, to obtain the organic fertilizer. The dryer is operated at a temperature of 80° C. to 160° C. The dry solid content of the organic fertilizer is 50% to 80%, calculated from the total weight of the organic fertilizer. The vapor released from the dryer may be fed to the stillage multi-effect evaporation system to provide thermal energy to the multi-effect evaporation system. After drying, the mixture of the solid part and the concentrated stillage is dried and this dried mixture can be used as the organic fertilizer.

The organic fertilizer contains the organic matter, protein, potassium salts, phosphate, the mineral substance and others. The organic matter content of the organic fertilizer is 30% to 65%, calculated from the total dry matter of the organic fertilizer. Total nutrient (calculated based on the formula that the nutrient=Nitrogen+Phosphorus pentoxide+potassium oxide) content of the organic fertilizer is 5% to 30%, calculated from the total dry matter of the organic fertilizer. The pH value of the organic fertilizer is 5.5 to 8.5. The water content of the organic fertilizer is 20% to 50%, calculated from the total weight of the organic fertilizer.

EXAMPLES

Example 1

Organic Acid Recovery from Cellulosic Pulps

Corn straw was used as the lignocellulosic raw material. Cellulosic pulp was obtained according to the organic acid pretreatment process. The organic acids composition is formic acid 26%, acetic acid content 59%, and 15% water, the temperature is 103° C., the solvation time is 240 min. After separation, the cellulosic pulp is separated from the liquid fraction.

Approximately 5 kg of cellulosic pulp was recovered, the dry matter content was 38.0%, the content of the organic acids was 49.5% and the content of water was 12.5%, calculated from the total weight of the cellulosic pulp. The cellulosic pulp was fed to the dryer to obtain the dried cellulosic pulp, the drying temperature was 120° C. After drying, the organic acids content of the dried cellulosic pulp was 5.5%.

The dried cellulosic pulp was introduced into the desolventizer at a feed flowrate is 200 g/min, direct steam is introduced into the bottom of the desolventizer, the temperature of the steam was 120° C., and the flowrate of the direct steam feed to the desolventizer was 14.1 g/min. The desolventized cellulosic pulp was discharged from the desolventizer.

The organic acids content of the desolventized cellulosic pulp was 1.8%, calculated from the total weight of the desolventized cellulosic pulp.

A second cellulosic pulp derived from corn straw was prepared under the similar conditions as described above. In this trial however the dryer temperature was slightly lower (110° C.) while the flowrate of steam in the desolventizer was increased to 26.3 g/min. The desolventized cellulosic pulp produced under these conditions had an organic acids content of 1.95%.

In a third study wheat straw was used as the lignocellulosic raw material and a cellulosic pulp was obtained according to the organic acid pretreatment process described above.

Approximately 5 kg of cellulosic pulp was recovered, the dry matter content was 37.5%, the content of organic acids was 50.2% and the content of water was 12.3%, calculated from the total weight of the cellulosic pulp. The cellulosic pulp was fed to the dryer to obtain the dried cellulosic pulp, the drying temperature was 115° C. After drying, the organic acids content of the obtained dried cellulosic pulp was 6.7%.

The dried cellulosic pulp was introduced into the desolventizer at a feed flowrate is 200 g/min, direct steam is introduced into the bottom of the desolventizer, the temperature of the steam was 120° C., and the flowrate of the direct steam feed to the desolventizer was 16.8 g/min. The desolventized cellulosic pulp is discharged from the desolventizer.

The desolventized cellulosic pulp produced under these conditions had an organic acids content of 1.91%.

Table 1 summarizes these data.

TABLE 1

Organic acid content of cellulosic pulps

| | Cellulosic pulp | | Dried cellulosic pulp | Desolventized cellulosic pulp | |
|---|---|---|---|---|---|
| | Dry matter content (%) | Organic acids content (%) | Water content (%) | Organic acids content (%) | Organic acids content (%) | Direct steam Flowrate (g/min) |
| Corn straw | 38 | 49.5 | 12.5 | 5.5 | 1.80 | 14.1 |
| Corn straw | 38 | 49.5 | 12.5 | 8.0 | 1.95 | 26.3 |
| Wheat straw | 37.5 | 50.2 | 12.3 | 6.7 | 1.91 | 16.8 |

Example 2

Neutralization and Alkalization Treatment of Cellulose.

Sample 1
Method A:

Initially, 0.4 kg cellulose (lignin content was 4.1% and organic acids content was 1.56%) was fed to the reactor, the agitator was started and the pH adjusted to 12 with a sodium hydroxide solution, which added 3.34 L of additional water. The temperature of the reactor was maintained at 80° C. and the reaction continued for 60 minutes.

When the reaction is ended, 9.16 g sodium hydroxide was consumed and the lignin content of the treated cellulose was 1.89%.

Method B:

In the initial neutralization step of a first processing run, 0.4 kg cellulose (lignin content was 4.1% and organic acids content was 1.56%) was fed to the reactor, the agitator was started and the pH adjusted to pH 6.5 with a sodium hydroxide solution, which added 3.34 L of additional water. The temperature of the reactor was maintained at 80° C. and the reaction continued for 30 minutes. Following this reaction, the cellulose mixture was filtered and pressed.

In the alkalizing step the neutralized cellulose is added to an alkalization reactor, the agitator is started, and the pH adjusted to pH 12 with a sodium hydroxide solution, which added 3.34 L of additional water. The temperature of the reactor was maintained at 80° C. and the reaction continued for 30 minutes. Sodium hydroxide was added as necessary to maintain the pH at pH 12. After 30 minutes the alkalized cellulose mixture was filtered and pressed to obtain the sodium hydroxide liquor and the alkalized cellulose. The sodium hydroxide liquor may be reused in the neutralization step in a second (subsequent) processing operations.

In a second processing run 0.4 kg of cellulose (with a lignin content of 4.1% and an organic acids content of 1.56%) is fed into the neutralization reactor, the agitator is started, and the sodium hydroxide liquor recovered from the alkalizing step of the first processing run is used to adjust the pH to pH 6.8, the temperature of the reactor is maintained at 80° C. and the reaction continued for 30 minutes. Following this reaction, the cellulose mixture was filtered and pressed.

The alkalizing step of the second (and subsequent) processing runs comprise the same as the steps described in the first round. Importantly, the sodium hydroxide liquor recovered after filtering and pressing the alkalized cellulose may be reused in the neutralization step in the next processing operation. In the second round of processing utilizing sodium hydroxide recovered from the first round the total sodium hydroxide consumed was 4.58 g, the lignin content of the treated cellulose was 1.85%.

Sample 2
Method A:

Initially, 0.4 kg cellulose (lignin content was 3.6% and organic acids content was 2.68%) was fed to the reactor, the agitator was started and the pH adjusted to 12 with a sodium hydroxide solution, which added 3.34 L of additional water. The temperature of the reactor was maintained at 80° C. and the reaction continued for 60 minutes.

When the reaction is ended 12.4 g sodium hydroxide was consumed and the lignin content of the treated cellulose was 1.56%.

Method B:

In the initial neutralization step of a first processing run, 0.4 kg cellulose (lignin content was 3.6% and organic acids content was 2.68%) was fed to the reactor, the agitator was started and the pH adjusted to pH 6.5 with a sodium hydroxide solution, which added 3.34 L of additional water. The temperature of the reactor was maintained at 80° C. and the reaction continued for 30 minutes. Following this reaction, the cellulose mixture was filtered and pressed.

In the alkalizing step the neutralized cellulose is added to an alkalization reactor, the agitator is started, and the pH adjusted to pH 12 with a sodium hydroxide solution, which added 3.34 L of additional water. The temperature of the reactor was maintained at 80° C. and the reaction continued for 30 minutes. Sodium hydroxide was added as necessary to maintain the pH at pH 12. After 30 minutes the alkalized cellulose mixture was filtered and pressed to obtain the sodium hydroxide liquor and the alkalized cellulose. The sodium hydroxide liquor may be reused in the neutralization step in subsequent processing operations.

In a second processing run 0.4 kg of cellulose (with a lignin content of 3.6% and an organic acids content of 2.68%) is fed into the neutralization reactor, the agitator is started, and the sodium hydroxide liquor recovered from the alkalizing step of the first processing run is used to adjust the pH to pH 6.8, the temperature of the reactor is maintained at 80° C. and the reaction continued for 30 minutes. Following this reaction, the cellulose mixture was filtered and pressed.

The alkalizing step of the second (subsequent) processing run comprises the same steps described in the first round. Importantly, the sodium hydroxide liquor recovered after filtering and pressing the alkalized cellulose may be reused in the neutralization step in the next processing operation. In the second round of processing utilizing sodium hydroxide recovered from the first round the total sodium hydroxide consumed was 7.87 g, the lignin content of the treated cellulose was 1.58%.

Sample 3
Method A:
Initially, 0.4 kg cellulose (lignin content was 3.8% and organic acids content was 4.52%) was fed to the reactor, the agitator was started and the pH adjusted to pH 12 with a sodium hydroxide solution, which added 3.34 L of additional water. The temperature of the reactor was maintained at 80° C. and the reaction continued for 60 minutes.

When the reaction is ended 17.9 g sodium hydroxide was consumed and the lignin content of the treated cellulose was 1.66%.

Method B:
In the initial neutralization step of a first processing run, 0.4 kg cellulose (lignin content was 3.8% and organic acids content was 4.52%) was fed to the reactor, the agitator was started and the pH adjusted to 6.5 with a sodium hydroxide solution, which added 3.34 L of additional water. The temperature of the reactor was maintained at 80° C. and the reaction continued for 30 minutes. Following this reaction, the cellulose mixture was filtered and pressed.

In the alkalizing step the neutralized cellulose is added to an alkalization reactor, the agitator is started, and the pH adjusted to pH 12 with a sodium hydroxide solution, which added 3.34 L of additional water. The temperature of the reactor was maintained at 80° C. and the reaction continued for 30 minutes. Sodium hydroxide was added as necessary to maintain the pH at pH 12. After 30 minutes the alkalized cellulose mixture was filtered and pressed to obtain the sodium hydroxide liquor and the alkalized cellulose. The sodium hydroxide liquor may be reused in the neutralization step in subsequent processing operations.

In a second (subsequent) processing run 0.4 kg of cellulose (with a lignin content of 3.8% and an organic acids content of 4.52%) is fed into the neutralization reactor, the agitator is started, and the sodium hydroxide liquor recovered from the alkalizing step of the first processing run is used to adjust the pH to pH 7.1, the temperature of the reactor is maintained at 80° C. and the reaction continued for 30 minutes. Following this reaction, the cellulose mixture was filtered and pressed.

The alkalizing step of the second (subsequent) processing run comprises the same steps described in the first round. Importantly, the sodium hydroxide liquor recovered after filtering and pressing the alkalized cellulose may be reused in the neutralization step in the next processing operation. In the second round of processing utilizing sodium hydroxide recovered from the first round the total sodium hydroxide consumed was 13.3 g, the lignin content of the treated cellulose was 1.63%.

Table 2 summarizes these sample data.

Example 3

Lignin Production
Extraction liquor was obtained from the organic acid pretreatment process, wherein the composition of the organic acids in the pretreatment comprises formic acid 26%, acetic acid content 59%, and water 15%. The pretreatment temperature was 103° C. and the pretreatment extraction duration was 240 min. After separation, the extraction liquor was separated from the solid fraction, the extraction liquor was concentrated by evaporation, and the concentrated extraction liquor obtained. The dry matter content of the concentrated extraction liquor was 60.1%, and the lignin content was 29.5% (the other components of the concentrated extraction liquor are listed in Table 3).

1.40 kg of concentrated extraction liquor was combined with an equal weight of the fresh water (1.40 kg) and an emulsifier (SHW300R lab emulsifier, Shanghai Shenghaiwei Electric Instruments Co., Ltd) operated at 7500 rpm for about 30 min was used to produce a lignin suspension. The lignin suspension was introduced into a centrifuge, centrifuged for 5 mins, and the first centrifugate (2.05 kg of liquid) and a solid lignin layer obtained. The first centrifugate is removed from the centrifuge.

1.94 kg of wash water was fed into a spray device to wash the lignin layer within the centrifuge. The washing water in the procedure includes water and mixtures of formic acid, acetic acid and water. When feeding the washing water to the centrifuge, an initial feed of 0.54 kg of high organic acids content washing water comprising an organic acid content of 5.92% was used, the second wash comprised 1.00 kg of low organic acids content washing water wherein the organic acid content was 0.8%, and a finally wash comprising 0.40 kg of fresh water was found to wash the lignin layer sufficiently to obtain pure lignin.

Following the initial centrifugation and discharge of the initial centrifugate, the centrifuge continued to operate for 5 min, during this time the first wash with high organic acids water was performed and the second centrifugate (0.54 kg) obtained. The centrifuge was operated for another 5 mins during which time the second wash with low organic acids water was performed and the third centrifugate 1.40 kg was obtained. After a subsequent third wash with fresh water a lignin layer comprising 0.75 kg was obtained. The first centrifugate and the second centrifugate were recovered and may be incorporated in subsequent hemicellulosic juice production unit operations. The dry lignin was discharged from the centrifuge, and the purity of the lignin determined to be 98.1% (the components of the lignin at each stage of operation are shown in Table 3).

TABLE 2

Sodium hydroxide consumption for treating cellulose

| | Cellulose | | | Sodium hydroxide consumption | | |
|---|---|---|---|---|---|---|
| | Acid content before treatment (%) | Lignin content before treatment (%) | Lignin content after treatment (%) | Sodium hydroxide consumption of Plan A (g) | Sodium hydroxide consumption of Plan B (g) | Reduced ratio (%) |
| Sample 1 | 1.56 | 4.1 | 1.85 | 9.16 | 4.58 | 50.0% |
| Sample 2 | 2.68 | 3.6 | 1.56 | 12.4 | 7.87 | 36.5% |
| Sample 3 | 4.52 | 3.8 | 1.63 | 17.9 | 13.3 | 25.7% |

TABLE 3

Components of concentrated extraction liquor, washing waters, and lignin (I)

| | Concentrated extraction liquor | Washing water | | | Lignin | Purity of dry lignin |
|---|---|---|---|---|---|---|
| | | H-water | L-water | $H_2O$ | | |
| Lignin | 29.54% | | | | 55.00% | 98.1% |
| $H_2O$ | 5.11% | 94.09% | 99.20% | 100.00% | 43.96% | |
| Cellulose | 3.00% | | | | 0.03% | |
| Xylan | 8.70% | | | | 0.10% | |
| Mineral | 6.07% | | | | 0.07% | |
| Others | 12.75% | | | | 0.14% | |
| Acetic acid | 23.75% | 5.87% | 0.80% | | 0.57% | |
| Formic acid | 11.08% | 0.05% | | | 0.13% | |
| Total Impurity | 65.35% | 5.92% | 0.80% | | 1.04% | |

Note:
impurities include cellulose, xylan, trace mineral, acetic acid and formic acid.

The third centrifugate (1.40 kg) from above was recycled for use as diluent of the concentrated extraction liquor to produce a lignin suspension using the SHW300R lab emulsifier as described above. The obtained lignin suspension was introduced into the centrifuger and the centrifuger was operated as described above to yield a lignin layer of about 0.75 kg.

In this operation the first wash comprised 0.54 kg of high organic acids content wash water in which the organic acid content was about 10%. The second wash comprised 1.00 kg the low organic acids content wash water in which the organic acid content was about 2%, and a final wash comprising 0.40 kg of fresh water. All centrifuge operations and conditions were carried out as described above. As before, the first and second centrifugates may be recycled for use in subsequent hemicellulosic juice production unit operations. At the end of the operation the lignin is discharged from the centrifuge. In this instance the purity of the lignin was 97.2% (the components of the lignin at each stage of operation are shown in Table 4).

TABLE 4

Components of concentrated extraction liquor, washing waters, and lignin (II)

| | Concentrated extraction liquor | Washing water | | | Lignin | Purity of dry lignin |
|---|---|---|---|---|---|---|
| | | H-water | L-water | $H_2O$ | | |
| Lignin | 29.54% | | | | 55.00% | 97.2% |
| $H_2O$ | 5.11% | 90.00% | 98.00% | 100.00% | 43.40% | |
| Cellulose | 3.00% | | | | 0.04% | |
| Xylan | 8.70% | | | | 0.12% | |
| Mineral | 6.07% | | | | 0.08% | |
| Others | 12.75% | | | | 0.17% | |
| Acetic acid | 23.75% | 9.92% | 2.00% | | 1.03% | |
| Formic acid | 11.08% | 0.08% | | | 0.15% | |
| Total Impurity | 65% | 10% | 2% | 0% | 2% | |

Note:
impurities include cellulose, xylan, trace mineral, acetic acid and formic acid. H-water indicates high organic acids content wash water and L-water indicates low organic acids content wash water.

Once again, the third centrifugate (1.40 kg) from the operation described above was recycled to dilute the concentrated extraction liquor to produce a lignin suspension by treatment with the SHW300R lab emulsifier. The obtained lignin suspension was introduced into the centrifuger and the centrifuger was operated as described above to yield a lignin layer.

In this operation the first wash comprised 0.54 kg of high organic acids content wash water in which the organic acid content was 5.92. The second wash comprised 1.00 kg of low organic acids content washing water in which the organic acid content was 0.8%, and a final wash comprising 0.79 kg of fresh water. All centrifuge operations and conditions were carried out as described above. As before, the first and second centrifugates may be recycled for use in subsequent hemicellulosic juice production unit operations. At the end of the operation the lignin is discharged from the centrifuge. In this instance the purity of the lignin was 98.8% (the components of the lignin at each stage of operation are shown in Table 5).

TABLE 5

Components of concentrated extraction liquor, washing waters, and lignin (III).

| | Concentrated extraction liquor | Washing water | | | Lignin | Purity of dry lignin |
|---|---|---|---|---|---|---|
| | | H-water | L-water | $H_2O$ | | |
| Lignin | 29.54% | | | | 55.00% | 98.8% |
| $H_2O$ | 5.11% | 94.09% | 99.20% | 100.00% | 44.34% | |
| Cellulose | 3.00% | | | | 0.02% | |
| Xylan | 8.70% | | | | 0.06% | |
| Mineral | 6.07% | | | | 0.04% | |
| Others | 12.75% | | | | 0.09% | |
| Acetic acid | 23.75% | 5.87% | 0.80% | | 0.36% | |
| Formic acid | 11.08% | 0.05% | | | 0.08% | |
| Total Impurity | 65.35% | 5.92% | 0.80% | | 0.66% | |

Note:
impurities include cellulose, xylan, trace mineral, acetic acid and formic acid. H-water indicates high organic acids content wash water and L-water indicates low organic acids content wash water.

Example 4

Hemicellulosic Juice Processing

A concentrated hemicellulosic mixture was obtained from an initial hemicellulosic mixture comprising dissolved hemicellulose, organic acids water, and other soluble constituents (16.4% dry matter content, 6.0% formic acid, 14.4% acetic acid, and 63.2% water) by use of an evaporator (100 mm diameter, 2 m height), using indirect steam to heat the evaporator to evaporate the organic acids and water from the hemicellulosic mixture.

The flowrate of the hemicellulosic mixture into the evaporator was 10.0 kg/h, with an indirect steam flowrate of 6.2 kg/h, and an evaporation temperature of 90° C., which produced a flowrate of the concentrated hemicellulosic mixture of 2.96 kg/h. The dry matter content of the concentrated hemicellulosic mixture produced under these conditions was 55.6%. The acids content of the concentrated hemicellulosic mixture was 16.5%.

Feeding the resulting concentrated hemicellulosic mixture into the top of a stripping column (100 mm diameter, 2.5 m height), and feeding the direct steam into the bottom of the stripping column, served to partially strip the organic acids present in the concentrated hemicellulosic into the direct steam. This produces the stripped hemicellulosic mixture. Adjusting the stripping specifications to a direct steam flowrate of 1.51 kg/h and a direct steam temperature of 105° C. produced a flowrate of the stripped hemicellulosic mixture of 2.46 kg/h. The dry matter content of the stripped hemicellulosic mixture was 60.4%. The acids content of the stripped hemicellulosic mixture was 1.64%.

Modeling the evaporation and stripping process with Aspen Plus software (Aspen Technology, Inc., Massachusetts, USA) allowed a number of different operational parameters to be explored based on regression of the vapor-liquid equilibrium with experimental data described above.

Using the model parameters described above, conditions and performance for 2, 3 and 4 effects evaporation and stripping systems were simulated for concentration of hemicellulosic mixture comprising dissolved hemicellulose, organic acids, and water and other constituents.

The flowsheets for the 2, 3, and 4 effects evaporation and stripping system are constructed for use by the Aspen Plus software, are shown in FIGS. 6-8, respectively. In these models the hemicellulosic mixture (21) comprising dissolved hemicellulose, organic acids, water and other constituents is evaporated by evaporator II and evaporator I and the concentrated hemicellulosic juice (22) is obtained. The concentrated hemicellulosic juice (22) is fed to the top of the stripping column (102), fresh steam (26) is fed to the bottom of the stripping column (102) and the stripped hemicellulosic juice (24) is obtained. The vapor discharged from the top of the stripping columns and the additional fresh steam (27) is used as a heat resource for evaporator I and the vapor discharged from the top of the stripping column and the additional fresh steam (27) that is condensed within evaporator I is recovered as condensed acid II (25). The vapor from evaporator I is used as a heat source for evaporator II, while the vapor from evaporator I that condenses in evaporator II serves as condensed acid I (23). The same scenario involving use of vapor initially recovered from the stripping column into evaporator I and vapor recovered from evaporator I serving as a heat source for evaporator II extends to systems that include additional multi-effect evaporator units as illustrated in FIG. 7 for a 3-effect evaporator system and FIG. 8 for a 4-effect evaporator system, there is no need of fresh steam in FIG. 7 for a 3-effect evaporator system, the more vapor (28) from the stripping column than the vapor needed for the 4-effect evaporator system is discharged from the top of the stripping column is used to the other system.

The tables below present many of the observed and predicted parameters of each of the multi-effect evaporator systems described herein.

TABLE 6

Observed inputs to the evaporation system models

|  | Flowrate (t/h) | Dry matter content (%) | Formic acid content (%) | Acetic acid content (%) | Water content (%) |
|---|---|---|---|---|---|
| The hemicellulosic mixture | 12.0 | 16.4% | 6.0% | 14.4% | 63.2% |

TABLE 7

Observed specification of the stripped hemicellulose juice

| Evaporation effects | Flowrate (t/h) | Dry matter content (%) | Total acids content (%) | Water content (%) |
|---|---|---|---|---|
| 2 | 3.27 | 60.2% | 0.53% | 39.27% |
| 3 | 3.25 | 60.5% | 1.65% | 37.85% |
| 4 | 3.27 | 60.1% | 0.93% | 38.97% |

TABLE 8

Predicted steam consumption of evaporation and stripping systems

|  | 2 effects | 3 effects | 4 effects |
|---|---|---|---|
| Steam consumption of stripping (t/h) | 3.85 | 2.75 | 3.23 |
| Steam consumption of evaporation (t/h) | 3.85 | 2.63 | 2.01 |
| Surplus steam (t/h) | 0 | 0.12 | 1.22 |

TABLE 9

Predicted heat exchange surface area of evaporation systems

|  | 2 effects | 3 effects | 4 effects |
|---|---|---|---|
| Total heat exchange surface (m²) | 887 | 1377 | 2269 |

Example 5

Recovering Organic Acids from High Water Content Organic Acids Solutions

A high water content organic acids solution (27.6% formic acid, 51.5% acetic acid, and 20.9% water) was fed into a distillation column (90 mm diameter, 3 m height, packing column) operating with a heat duty of 12.6 MJ/h, a reflux ratio of 13.0, 1 atmosphere pressure, at a flow rate of 4.0 kg/h. Under these conditions the condensate of the vapor released from the top of the column is produced at a flow rate of 0.41 kg/h which comprises 0.27% formic acid, 4.07% acetic acid, and 95.66% water. The distilled organic acids solution, which is discharged from the column bottom, is obtained at a flow rate of 3.59 kg/h and comprises 30.7% formic acid, 56.9% acetic acid, and 12.4% water.

Modeling this process with the Aspen Plus software using the parameters described above allows simulation of distillation systems comprising 2, 3, 4, and 5 columns for separating water from high water content organic acids solutions. The flow sheets produced by the modelling software are shown in FIGS. 10-13 for 2-column, 3-column, 4-column, and 5-column distillation systems, respectively.

The organic acids composition of the various input streams of high water content organic acids solutions originating from organic acids pretreatment processes are listed in Table 10.

TABLE 10

Organic acid composition of inputs to multi-column distillation systems

| Stream | Flowrate (kg/h) | Formic acid content (%) | Acetic acid content (%) | Water content (%) |
|---|---|---|---|---|
| 1 | 471.3 | 27.6% | 49.1% | 23.3% |
| 2 | 270.7 | 5.8% | 15.2% | 79.0% |
| 3 | 80.6 | 7.6% | 17.4% | 75.0% |
| 4 | 12.8 | 9.9% | 18.9% | 71.2% |

Note:
The stream designation matches those depicted in FIG. 10 and described below.

Figure 10:
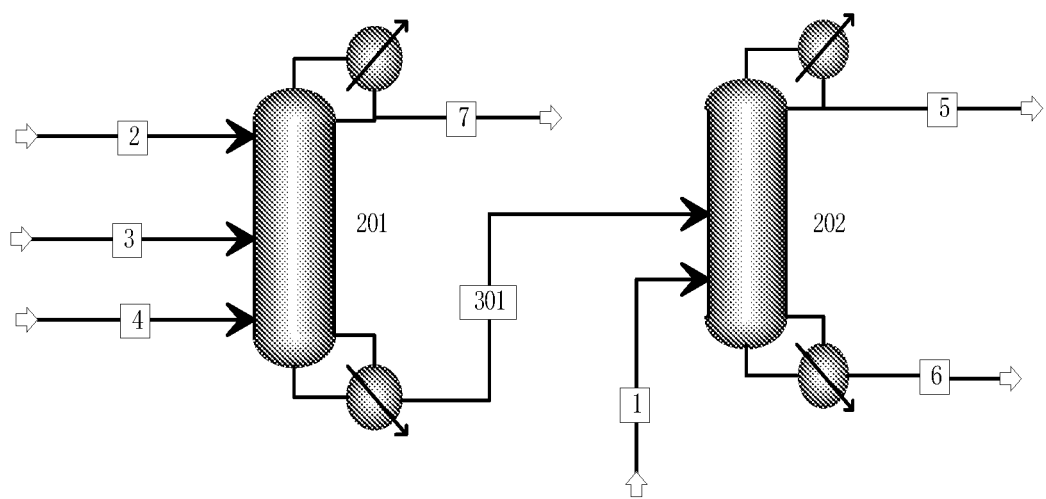
FIG. 10 illustrates the details of a 2 column distillation system. Internal labels are described in Example 5.

The basic distillation process for a 2 column distillation system is illustrated in FIG. 10. Three of the four input streams are fed into are fed into the first distillation column (201). These streams are derived from the hemicellulosic juice evaporation step (2), the hemicellulosic juice stripping step (3), and the high water organic acids solution from the desolventizer step of cellulosic pulp processing (4). The condensate of vapor (7) discharged from the top of the first column (201) may be recovered for other unit operations. The concentrated mixture (301) is discharged from the bottom of the first column (201) and fed into column 2 (202). The remaining input stream (1) derived from the extracting liquor evaporation step of lignin production is also fed into column 2 (202). The condensate of vapor (5) discharged from the top of the second column (202) may be recovered for other unit operations. The distilled organic acids solution (6) is discharged from the bottom of the second column (202). The organic acid content of the various output streams of a two-column distillation system are presented in Table 11.

TABLE 11

Organic acid composition of outputs of a 2-column distillation system

| Stream | Flowrate (kg/h) | Formic acid content (%) | Acetic acid content (%) | Water content (%) |
|---|---|---|---|---|
| 5 | 129.8 | 0.0% | 0.8% | 99.2% |
| 6 | 477.8 | 32.0% | 60.0% | 8.0% |
| 7 | 227.8 | 0.0% | 0.8% | 99.2% |

Note:
The stream designation matches those depicted in FIG. 10 and described above.

Figure 11:
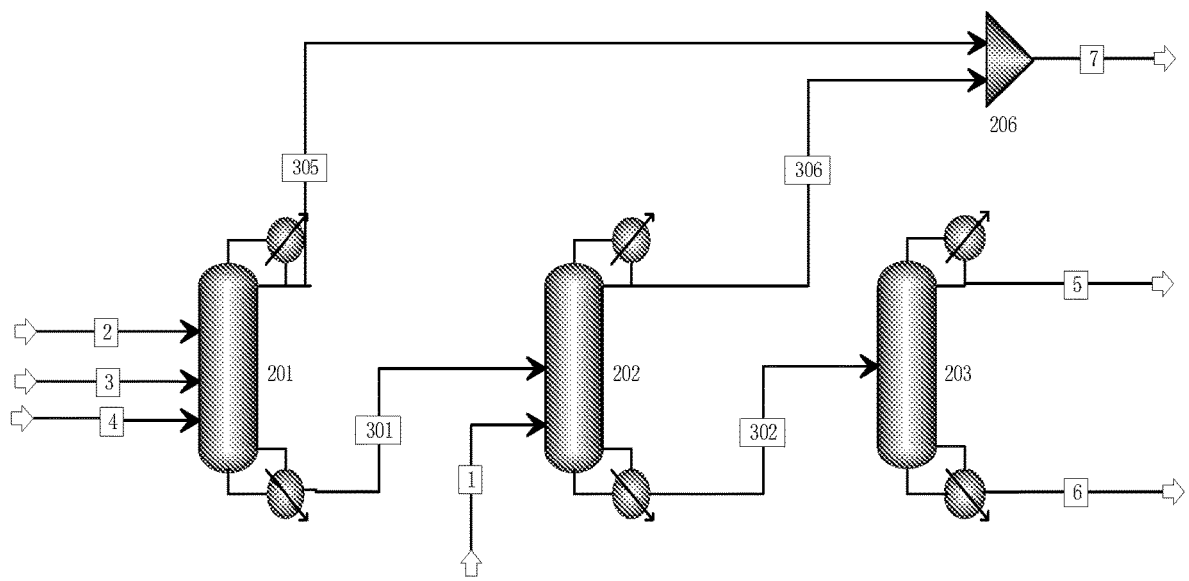
FIG. 11 illustrates the details of a 3 column distillation system. Internal labels are described in Example 5.

A similar process representing the process flow within a 3 column distillation system is depicted in FIG. 11. In this case the operation is similar in terms of input and output streams of the two column system described above. However, in this case the vapor condensates of the first two columns are pooled to form a single output stream (7 of FIG. 11) and the distilled organic acids solution discharged from column 2 (302) is fed into a third column (203) where the vapor condensate (5) is recovered and the further distilled organic acids solution (6) is discharged from the bottom of the third column (203). The organic acid content of the various output streams of a two-column distillation system are presented in Table 12.

TABLE 12

Organic acid composition of outputs of a 3-column distillation system

| Stream | Flowrate (kg/h) | Formic acid content (%) | Acetic acid content (%) | Water content (%) |
|---|---|---|---|---|
| 5 | 78.4 | 0.0% | 0.8% | 99.2% |
| 6 | 477.8 | 32.0% | 60.0% | 8.0% |
| 7 | 279.3 | 0.0% | 0.8% | 99.2% |

Note:
The stream designation matches those depicted in FIG. 11 and described above.

Figure 12:
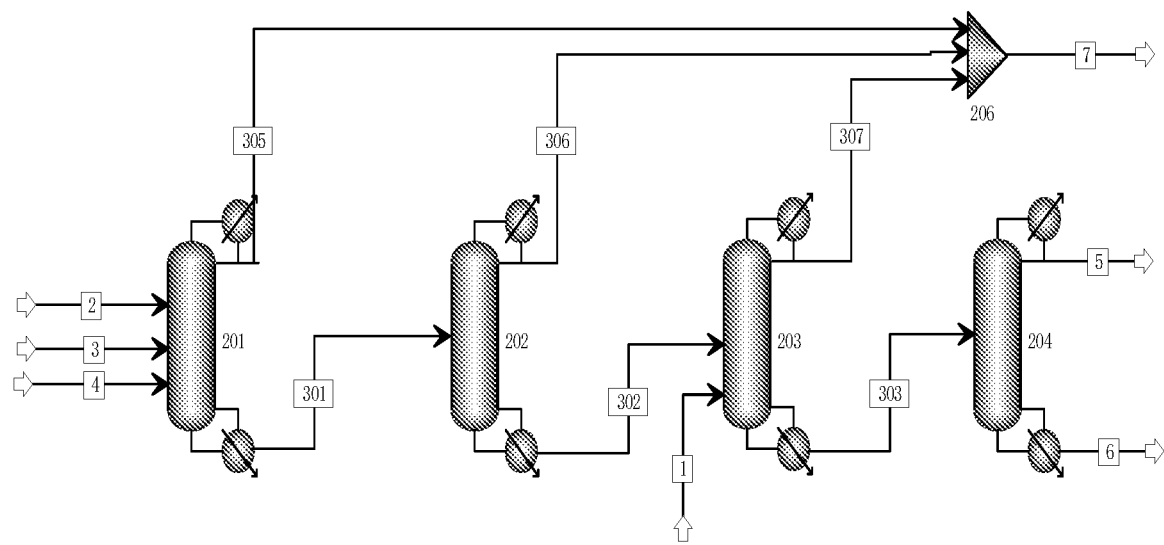
FIG. 12 illustrates the details of a 4 column distillation system. Internal labels are described in Example 5.

Similarly, the process representing the process flow within a 4 column distillation system is depicted in FIG. 12. The organic acid content of the various output streams of a two-column distillation system are presented in Table 13.

TABLE 13

Organic acid composition of outputs of a 4-column distillation system

| Stream | Flowrate (kg/h) | Formic acid content (%) | Acetic acid content (%) | Water content (%) |
|---|---|---|---|---|
| 5 | 49.8 | 0.0% | 0.8% | 99.2% |
| 6 | 477.8 | 32.0% | 60.0% | 8.0% |
| 7 | 307.8 | 0.0% | 0.8% | 99.2% |

Note:
The stream designation matches those depicted in FIG. 12.

Figure 13:
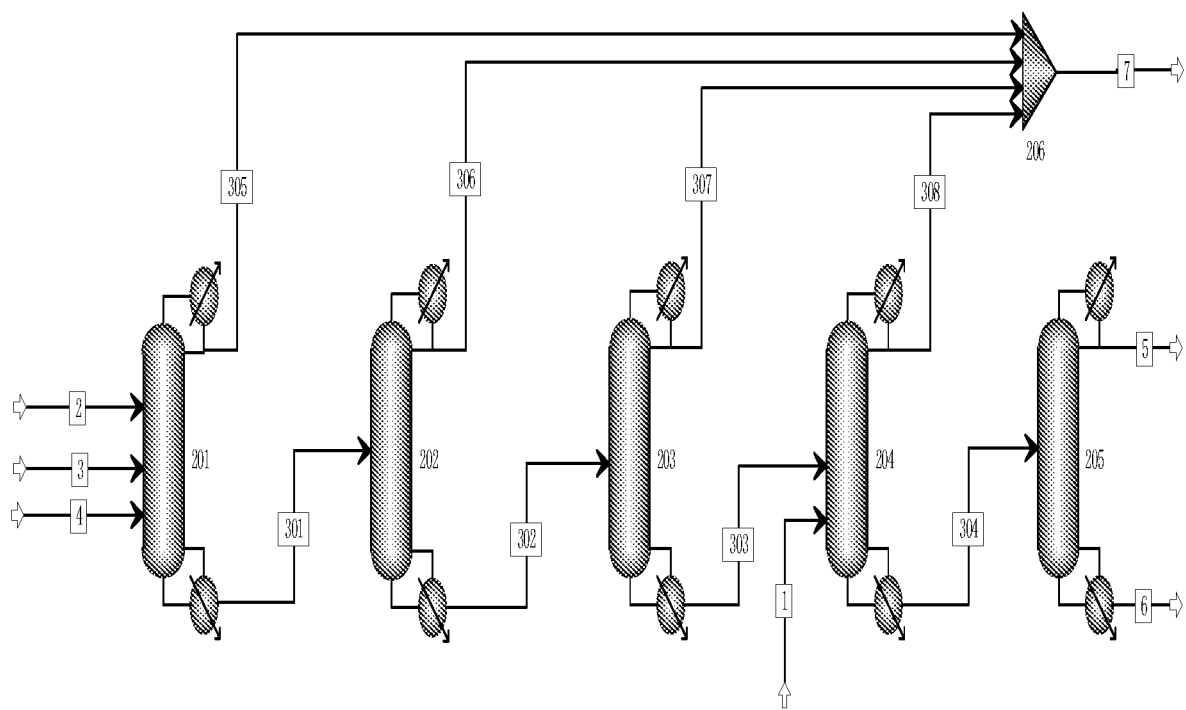
FIG. 13 illustrates the details of a 5 column distillation system. Internal labels are described in Example 5.

The process representing the process flow within a 5 column distillation system is depicted in FIG. 13. The organic acid content of the various output streams of a five-column distillation system are presented in Table 14.

TABLE 14

Organic acid composition of outputs of a 5-column distillation system

| Stream | Flowrate (kg/h) | Formic acid content (%) | Acetic acid content (%) | Water content (%) |
|---|---|---|---|---|
| 5 | 37.5 | 0.0% | 0.8% | 99.2% |
| 6 | 477.8 | 32.0% | 60.0% | 8.0% |
| 7 | 320.2 | 0.0% | 0.8% | 99.2% |

Note:
The stream designation matches those depicted in FIG. 12.

According to the simulation flow sheets steam consumption can be significantly reduced by the number of distillation columns present in the system. The data supporting this observation is presented in Table 15.

TABLE 15

Steam consumption profiles of 2-, 3-, and 4-column distillation systems

| Type | Heat duty (MJ/h) | Reduced ratio (%) |
|---|---|---|
| 2 column distillation | 1188 | 27.6% |
| 3 column distillation | 860.4 | |
| 3 column distillation | 860.4 | 20.0% |
| 4 column distillation | 687.6 | |

The indicated reduction in the thermal requirements of a two column system relative to three column system is 27.6%, while the reduction in the thermal requirements of a four column system are an additional 20% lower than those of three column system, with an overall reduction to 42% of the thermal requirements of a two column system required for a four column system.

Interestingly, additional columns provide minimal energy improvements. See Table 16.

TABLE 16

Steam consumption profiles of 4- and 5-column distillation systems

| Type | Heat duty (MJ/h) | Reduced ratio (%) |
|---|---|---|
| 4 column distillation | 687.6 | 4.97% |
| 5 column distillation | 653.4 | |

Example 6

Organic Fertilizer

In an initial experiment, corn straw was used as the lignocellulosic plant material source for organic acids treatment using formic acid and acetic acid to extract the hemicellulose and the lignin. The mixture of hemicellulose and lignin was separated to obtain a cellulosic pulp fraction and an extraction liquor. The cellulosic pulp was treated to partially eliminate lignin and washed with water to obtain cellulose. The extraction liquor was concentrated to separate the lignin, after the separation of the lignin, the residue was concentrated and stripped to obtain the hemicellulosic juice. The cellulose and hemicellulosic juice mixture was hydrolyzed and fermented of by adding cellulose enzymes and yeast, respectively, to produce ethanol. The ethanol was separated from the fermentate by distillation, the residual matter of the distillation constitutes the stillage.

Stillage (2113 g comprising 9.23% dry matter content) was fed into a decanter to produce a solid fraction 61.4 g (comprising 38.0% dry matter content) and a thin stillage 2051.6 g (comprising 8.37% dry matter content) after decanting. The thin stillage was evaporated (in an evaporator operated at 110° C.) to obtain the concentrated stillage 451.6 g (comprising 38.0% dry matter content). The solid fraction and concentrated stillage were combined to obtain a mixture (513.0 g). The mixture was dried in a dryer operated at a temperature of 120° C. to obtain 335.1 g of a final organic fertilizer; with a dry matter content of organic fertilizer of 58.2% and a pH of 6.1. The organic fertilizer has a dry matter content of 58.2%, an organic matter content of 47.8%, and a total nutrient content of 5.86% (calculated based on a formula wherein Nutrient=Nitrogen+Phosphorus pentoxide+Potassium oxide), calculated from the total dry matter.

In a second trial to produce an organic fertilizer from stillage using corn straw as an initial input to the organic acids treatment process, stillage (2113 g comprising 9.23% dry matter) was fed into the decanter. After decanting a solid fraction 67.1 g (35.5% dry matter content) and a thin stillage 2046 g (8.37% dry matter content) were obtained. The thin stillage was evaporated (in an evaporator operated at 105° C.) to produce 456.7 g of a concentrated stillage with 37.5% dry matter content. The solid fraction and the concentrated stillage were combined to produce 523.8 g of a mixture. The mixture was dried in a dryer operated at 130° C. to produce 297.7 g of the final organic fertilizer with a dry matter content of 65.5% at pH 6.0. The organic fertilizer contains 47.3% organic matter with a total nutrient content of 5.81%, calculated from the total dry matter.

In a third experiment to produce organic fertilizer from stillage, wheat straw was used as an initial input to the organic acids treatment process, stillage (1940 g comprising 9.38% dry matter) was fed into the decanter. After decanting a solid fraction 59.5 g (37.0% dry matter content) and a thin stillage 1880.5 g (8.51% dry matter content) were obtained. The thin stillage was evaporated (in an evaporator operated at 115° C.) to produce 438.3 g of a concentrated stillage with 36.5% dry matter content. The solid fraction and the concentrated stillage were combined to produce 497.8 g of a mixture. The mixture was dried in a dryer operated at 140° C. to produce 244.3 g of the final organic fertilizer with a dry matter content of 74.5% at pH 6.2. The organic fertilizer contains 48.5% organic matter with a total nutrient content of 6.12%, calculated from the total dry matter.

What is claimed is:

1. A method for producing a desolventized cellulosic pulp containing less than 2% organic acids, the method comprising the steps of:
   a) drying a cellulosic pulp produced from organic acids pretreatment of plant material in a dryer to remove the organic acids to a content of 3% to 18%, calculated from the total weight of the dried cellulosic pulp, and
   b) capturing vapor released from the dryer for use in the extraction liquor concentration system and other organic acids pretreatment operational systems as a source of thermal energy, and
   c) condensing the captured vapor in the extraction liquor concentration system to form a first phase of the organic acids solution of the organic acids pretreatment process, or optionally, using the vapor to provide thermal energy to additional operational steps within the organic acids pretreatment process, and
   d) using direct steam in a desolventizer to further remove the organic acids from the cellulosic pulp, and
   e) condensing the organic acids in the vapor released from the desolventizer, to obtain a second phase of organic acids solution of the organic acids pretreatment process.

2. The method according to claim 1, wherein the organic acids of the process comprise a mixture of formic acid, acetic acid and water.

3. The method according to claim 1, wherein the organic acids of the process comprise a mixture of formic acid, acetic acid, furfural and water.

4. The method according to claim 1, wherein the organic acids of the process comprise a mixture of formic acid, furfural and water.

5. The method according to claim 1, wherein the organic acids of the process comprise a mixture of formic acid and water.

6. The method according to claim 1, wherein the dryer of the process is a bulk dryer.

7. The method according to claim 6, wherein the bulk dryer is selected from the group consisting of tube dryer, pneumatic dryer and rotary disc dryer.

8. The method according to claim 7, wherein the bulk dryer is a tube dryer.

9. The method according to claim 1, wherein the dryer of the process is operated at a temperature of 80° C. to 160° C.

10. The method according to claim 1, wherein the first phase of the organic acids solution of the organic acids pretreatment process comprises an organic acids content of 50% to 95%, total weight relative to the first phase of organic acids solution recovered in step c) of the process.

11. The method according to claim 1, wherein the first phase of organic acids solution recovered in step c) of the process is reused in the organic acids pretreatment process.

12. The method according to claim 1, wherein the desolventizer uses direct steam at a temperature of 90° C. to 130° C.

13. The method according to claim 1, wherein the second phase of organic acids solution of the organic acids pretreatment process comprises an organic acids content of 5% to 60%, total weight relative to the second phase of organic acids solution in step e) of the process.

14. The method according to claim 1, wherein the second condensation system to recover the organic acids in step e) of the process comprises 1 to 3 condensers.

15. The method according to claim 1, wherein the second condensation system to recover the organic acids in step e) of the process comprises 2 condensers.

* * * * *